(12) United States Patent
Enoki et al.

(10) Patent No.: US 10,513,744 B2
(45) Date of Patent: Dec. 24, 2019

(54) **MARKER ASSOCIATED WITH RESISTANCE TO SMUT IN PLANT BELONGING TO GENUS *SACCHARUM*, AND USE THEREOF**

(71) Applicant: TOYOTA JIDOSHA KABUSHIKI KAISHA, Toyota-shi, Aichi (JP)

(72) Inventors: Hiroyuki Enoki, Okazaki (JP); Tatsuro Kimura, Kariya (JP); Satoru Nishimura, Nagoya (JP); Aya Murakami, Toyota (JP); Takayoshi Terauchi, Nishinoomote (JP); Takeo Sakaigaichi, Nishinoomote (JP); Taiichiro Hattori, Nishinoomote (JP); Shoko Ishikawa, Nishinoomote (JP); Yoshifumi Terajima, Ishigaki (JP)

(73) Assignee: TOYOTA JIDOSHA KABUSHIKI KAISHA, Toyota-shi, Aichi-ken (JP)

( * ) Notice: Subject to any disclaimer, the term of this patent is extended or adjusted under 35 U.S.C. 154(b) by 0 days.

(21) Appl. No.: 15/664,093

(22) Filed: Jul. 31, 2017

(65) Prior Publication Data
US 2017/0327907 A1    Nov. 16, 2017

Related U.S. Application Data

(62) Division of application No. 14/113,539, filed as application No. PCT/JP2012/060671 on Apr. 20, 2012, now Pat. No. 9,758,841.

(30) Foreign Application Priority Data

Apr. 28, 2011   (JP) ................................ 2011-101050
Apr. 18, 2012   (JP) ................................ 2012-094995

(51) Int. Cl.
| | | |
|---|---|---|
| *C12Q 1/68* | (2018.01) | |
| *A01H 1/04* | (2006.01) | |
| *C12Q 1/6895* | (2018.01) | |
| *A01H 5/04* | (2018.01) | |

(52) U.S. Cl.
CPC ............ *C12Q 1/6895* (2013.01); *A01H 1/04* (2013.01); *A01H 5/04* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 2009/0222941 A1 | 9/2009 | Taguchi et al. |
| 2010/0138950 A1 | 6/2010 | Ragot |
| 2011/0154528 A1 | 6/2011 | Ragot et al. |

FOREIGN PATENT DOCUMENTS

| | | |
|---|---|---|
| JP | 2010-516236 A | 5/2010 |
| WO | 2007/125958 A1 | 11/2007 |

OTHER PUBLICATIONS

Butterfield, 2007, PhD thesis "Marker Assisted Breeding in Sugarcane: A Complex Polyploid", University of Stellenbosch, pp. 1-75.*
Ji et al., "Comparative QTL Mapping of Resistance to Sporisorium reiliana in Maize Based on Meta-analysis of QTL Locations" 2007, vol. 8, No. 2, pp. 132-139.
Xu et al., "Identification of RAPD Marker Linked to SMUT Resistance Gene in Sugarcane", Chin J Appl Environ Biol, Jun. 25, 2004, vol. 10, No. 3, pp. 263-267, ISSN 1006-687X.
Piperidis et al., "Comparative genetics in sugarcane enables structured map enhancement and validation of marker-trait associations", Molecular Breeding, 2008, vol. 21, 233-247.
Pan, et al., "Molecular Genotyping of Sugarcane Clones with Microsatellite DNA Markers", Maydica, 2003, pp. 319-329, vol. 48.
De Setta et al., "Building the sugarcane genome for biotechnology and identifying evolutionary trends," BMC Genomics 15:540, 17pps. (2014).
Butterfield, "Marker Assisted Breeding in Sugarcane: a Complex Polyploid," Ph.D. Thesis, University of Stellenbosch, pp. 1-75 (2007).
Aitken et al., "A combination of AFLP and SSR markers provides extensive map coverage and identification of homo(eo)logous linkage groups in a sugarcane cultivar," Theor. Appl. Genet. 110:789-801 (2005).
Gupta et al., "Array-based high-throughput DNA markers for crop improvement," Heredity 101:5-18 (2008).
Aitken et al., "A comprehensive genetic map of sugarcane that provides enhanced map coverage and integrates high-throughput Diversity Array Technology (DArT) markers," BMC Genomics 15:152 (2014).
Restriction Requirement, dated Aug. 18, 2015, issued by the United States Patent and Trademark Office in U.S. Appl. No. 14/113,539.
Non-Final Office Action, dated Nov. 19, 2015, issued by the United States Patent and Trademark Office in U.S. Appl. No. 14/113,539.
Final Office Action, dated May 3, 2016, issued by the United States Patent and Trademark Office in U.S. Appl. No. 14/113,539.
Advisory Action, dated Aug. 9, 2016, issued by the United States Patent and Trademark Office in U.S. Appl. No. 14/113,539.
Non-Final Office Action, dated Sep. 28, 2016, issued by the United States Patent and Trademark Office in U.S. Appl. No. 14/113,539.
Final Office Action, dated Jan. 27, 2017, issued by the United States Patent and Trademark Office in U.S. Appl. No. 14/113,539.

(Continued)

*Primary Examiner* — Bratislav Stankovic
(74) *Attorney, Agent, or Firm* — Sughrue Mion, PLLC

(57) ABSTRACT

The present invention relates to a marker associated with resistance to smut which is a quantitative trait of sugarcane. Specifically, a marker associated with resistance to sugarcane smut, which consists of a continuous nucleic acid region existing in a region sandwiched between the nucleotide sequence shown in SEQ ID NO: 1 and the nucleotide sequence shown in SEQ ID NO: 14 or a different similar region, is provided.

4 Claims, 19 Drawing Sheets

Specification includes a Sequence Listing.

(56) References Cited

OTHER PUBLICATIONS

Notice of Allowance, dated May 19, 2017, issued by the United States Patent and Trademark Office in U.S. Appl. No. 14/113,539.
Ji et al., "Comparative QTL Mapping of Resistance to Sporisorium reiliana in MaizeBased on Meta-analysis of QTL Locations," Journal of Plant Genetic Resources, 2007, vol. 8, No. 2, pp. 132-139.
Communication, dated Sep. 10, 2018, issued by the United States Patent and Trademark Office in U.S. Appl. No. 15/664,114.
Communication, dated Sep. 4, 2018, issued by the United States Patent and Trademark Office in U.S. Appl. No. 15/664,139.
Communication, dated Nov. 29, 2018, issued by the United States Patent and Trademark Office in U.S. Appl. No. 15/664,114.
Communication, dated Dec. 10, 2018, issued by the United States Patent and Trademark Office in U.S. Appl. No. 15/664,139.
Communication, dated Mar. 26, 2019, issued by the United States Patent and Trademark Office in U.S. Appl. No. 15/664,139.
Communication, dated Mar. 15, 2019, issued by the United States Patent and Trademark Office in U.S. Appl. No. 15/664,114.
Communication, dated Aug. 20, 2019, issued by the United States Patent and Trademark Office in U.S. Appl. No. 15/664,139.
Communication, dated Aug. 1, 2019, issued by the United States Patent and Trademark Office in U.S. Appl. No. 15/664,114.

* cited by examiner

SEQUENCE LISTING

<160> NUMBER OF SEQ ID NOS: 88

<210> SEQ ID NO 1
<211> LENGTH: 50
<212> TYPE: DNA
<213> ORGANISM: Saccharum officinarum

<400> SEQUENCE: 1
cctcgtcatg cacccgtgcc tcttcttcct cttgctgttg ctcctcctcc          50

<210> SEQ ID NO 2
<211> LENGTH: 71
<212> TYPE: DNA
<213> ORGANISM: Saccharum officinarum

<400> SEQUENCE: 2
ggaattgttg tagatttgtt ttgtgatgga aagatcatac ctcagctaca agaagtaaat    60
atccttttcc a                                                          71

<210> SEQ ID NO 3
<211> LENGTH: 63
<212> TYPE: DNA
<213> ORGANISM: Saccharum officinarum

<400> SEQUENCE: 3
ggcattagaa gaaaggtgga agaataaggt ttgagcccctt atttatttgc tttggtgatg    60
gat                                                                     63

<210> SEQ ID NO 4
<211> LENGTH: 50
<212> TYPE: DNA
<213> ORGANISM: Saccharum officinarum

<400> SEQUENCE: 4
ccattctact tctaccaacc ataaaacagg aggagcatgc atgcacatgc          50

<210> SEQ ID NO 5
<211> LENGTH: 50

```
<212> TYPE: DNA
<213> ORGANISM: Saccharum officinarum

<400> SEQUENCE: 5
attgcttgct cgctgcaact tgggccatgt ttagttcctc gaatttgagt        50

<210> SEQ ID NO 6
<211> LENGTH: 65
<212> TYPE: DNA
<213> ORGANISM: Saccharum officinarum

<400> SEQUENCE: 6
agtgaagaga ttggatttct agggttactt tataaagtgt caacacctta gatctgtttt    60
ttagt                                                          65

<210> SEQ ID NO 7
<211> LENGTH: 50
<212> TYPE: DNA
<213> ORGANISM: Saccharum officinarum

<400> SEQUENCE: 7
ggccggcacg agcatcaggg tcaagactca agagctcaag tgcttgcttt        50

<210> SEQ ID NO 8
<211> LENGTH: 50
<212> TYPE: DNA
<213> ORGANISM: Saccharum officinarum

<400> SEQUENCE: 8
tactttgtct cgttccagta gtccatcaag caagcctcgt acacaagtcc        50

<210> SEQ ID NO 9
<211> LENGTH: 50
<212> TYPE: DNA
<213> ORGANISM: Saccharum officinarum

<400> SEQUENCE: 9
tgcactgggg ataccagttg agttgattgc acaacttgcg ctacaccatg        50

<210> SEQ ID NO 10
<211> LENGTH: 50
<212> TYPE: DNA
<213> ORGANISM: Saccharum officinarum

<400> SEQUENCE: 10
gccgcctgat ggaaacggtc gtcgcatcca aagacgcaca tggtttagca        50

<210> SEQ ID NO 11
<211> LENGTH: 57
<212> TYPE: DNA
<213> ORGANISM: Saccharum officinarum

<400> SEQUENCE: 11
agtacctgtt ctgctgcact acataacagt acttttcagt gaacgaacag tgttttc      57

<210> SEQ ID NO 12
<211> LENGTH: 50
<212> TYPE: DNA
<213> ORGANISM: Saccharum officinarum

<400> SEQUENCE: 12
agcggatagc gctagcatgt cattctctcc cctcgctagc acgttattcc        50
```

<210> SEQ ID NO 13
<211> LENGTH: 52
<212> TYPE: DNA
<213> ORGANISM: Saccharum officinarum

<400> SEQUENCE: 13
gttgcggcgt gtgttgatga tgtaaagaat actcgtccgt gagaaattat ca    52

<210> SEQ ID NO 14
<211> LENGTH: 50
<212> TYPE: DNA
<213> ORGANISM: Saccharum officinarum

<400> SEQUENCE: 14
acgtgacgac gacgacgatg cagctggggc ttggcgtgga atggttgtcg    50

<210> SEQ ID NO 15
<211> LENGTH: 65
<212> TYPE: DNA
<213> ORGANISM: Saccharum officinarum

<400> SEQUENCE: 15
ggccttgttt aaatgtcacc taaattctaa attttacact cttttcataa catcgaatct    60
taaaa    65

<210> SEQ ID NO 16
<211> LENGTH: 61
<212> TYPE: DNA
<213> ORGANISM: Saccharum officinarum

<400> SEQUENCE: 16
aaactgaggg attactttcc aattgaaatg tcatccacca caaacacaaa aggcatactc    60
a    61

<210> SEQ ID NO 17
<211> LENGTH: 50
<212> TYPE: DNA
<213> ORGANISM: Saccharum officinarum

<400> SEQUENCE: 17
acactacact gtgtaggcaa tgagcagctc tgttgcacag caaagccaaa    50

<210> SEQ ID NO 18
<211> LENGTH: 50
<212> TYPE: DNA
<213> ORGANISM: Saccharum officinarum

<400> SEQUENCE: 18
ggatgtgaag tatgtatgtg ttttcagatg gaccaaggaa gctgcatggg    50

<210> SEQ ID NO 19
<211> LENGTH: 68
<212> TYPE: DNA
<213> ORGANISM: Saccharum officinarum

<400> SEQUENCE: 19
tacggtggta caaagcttag atcaatgatc aagctacaaa acacacaaag atagtcagta    60
gaaaaagt    68

<210> SEQ ID NO 20
<211> LENGTH: 50

<210> SEQ ID NO 20
<211> LENGTH: 50
<212> TYPE: DNA
<213> ORGANISM: Saccharum officinarum

<400> SEQUENCE: 20
gacgacgagg tgggcagcgc cagtgcgcta ctaccttctt tcttgcaact          50

<210> SEQ ID NO 21
<211> LENGTH: 69
<212> TYPE: DNA
<213> ORGANISM: Saccharum officinarum

<400> SEQUENCE: 21
gtatggttat gttggtacta aaggtttctg actattgtat tgtattgttg tgttataatg   60
ggttcaatg                                                          69

<210> SEQ ID NO 22
<211> LENGTH: 50
<212> TYPE: DNA
<213> ORGANISM: Saccharum officinarum

<400> SEQUENCE: 22
ggctgcaata cctgttcctc atctcatcta ttcgtgcaaa gttgctggtc             50

<210> SEQ ID NO 23
<211> LENGTH: 50
<212> TYPE: DNA
<213> ORGANISM: Saccharum officinarum

<400> SEQUENCE: 23
tcgggttgga ggcaaggaag aaaggagcta gattgctcgg ctgctggtgc             50

<210> SEQ ID NO 24
<211> LENGTH: 50
<212> TYPE: DNA
<213> ORGANISM: Saccharum officinarum

<400> SEQUENCE: 24
acagtagtgc aactgcgacg acgatgtgtg ggtatatgtt ccatagcttg             50

<210> SEQ ID NO 25
<211> LENGTH: 50
<212> TYPE: DNA
<213> ORGANISM: Saccharum officinarum

<400> SEQUENCE: 25
ttttgattgg ccttgcagat gttgcagcga tggcactcgt ggcaaacaga             50

<210> SEQ ID NO 26
<211> LENGTH: 63
<212> TYPE: DNA
<213> ORGANISM: Saccharum officinarum

<400> SEQUENCE: 26
aaccatgctg aaaacgtctt ccgtttacag tttatggtat atccgcttaa aactaactcg   60
atc                                                                63

<210> SEQ ID NO 27
<211> LENGTH: 63
<212> TYPE: DNA
<213> ORGANISM: Saccharum officinarum

<400> SEQUENCE: 27

```
aatctaaatg actaatgaga ccgtgagagc tgcttagctt aatggtgcat cccttttaa    60 act                                                                63

<210> SEQ ID NO 28
<211> LENGTH: 58
<212> TYPE: DNA
<213> ORGANISM: Saccharum officinarum

<400> SEQUENCE: 28
aagaacactg ctaaggatgg tcacaatttg gaaactgaag ttttatctct ggttcggt    58

<210> SEQ ID NO 29
<211> LENGTH: 53
<212> TYPE: DNA
<213> ORGANISM: Saccharum officinarum

<400> SEQUENCE: 29
aagctgcatc tgattctcat ccaaacctgc tctgctcatt atcattactt cgt         53

<210> SEQ ID NO 30
<211> LENGTH: 50
<212> TYPE: DNA
<213> ORGANISM: Saccharum officinarum

<400> SEQUENCE: 30
ccaaccaaca gcaagaacac caagacgcac ataatgaggc ccatgaagta              50

<210> SEQ ID NO 31
<211> LENGTH: 64
<212> TYPE: DNA
<213> ORGANISM: Saccharum officinarum

<400> SEQUENCE: 31
tttacaccag tgaactgaca aaaaatcgaa gtggtgcggt acataagaac atttacatcc   60
aact                                                               64

<210> SEQ ID NO 32
<211> LENGTH: 73
<212> TYPE: DNA
<213> ORGANISM: Saccharum officinarum

<400> SEQUENCE: 32
gaccaatcta ggaaaaacaa ttgcacaaat gactacattt attatggcaa atcaattttc   60
ttcagtcatt gta                                                     73

<210> SEQ ID NO 33
<211> LENGTH: 58
<212> TYPE: DNA
<213> ORGANISM: Saccharum officinarum

<400> SEQUENCE: 33
atagtctacc tatactggtg ccacaagtca acaagtgatg gcaatacccca ttcaaatt    58

<210> SEQ ID NO 34
<211> LENGTH: 71
<212> TYPE: DNA
<213> ORGANISM: Saccharum officinarum

<400> SEQUENCE: 34
tggcaatacc cattcaaatt gcgtcaaatg tgaataaatg gaggtagatg actaacacct   60
ttgtttcaaa a                                                       71
```

<210> SEQ ID NO 35
<211> LENGTH: 50
<212> TYPE: DNA
<213> ORGANISM: Saccharum officinarum

<400> SEQUENCE: 35
ctgcaataca atgcggtgga agcggattgg tggaaggcat gcatgcatca         50

<210> SEQ ID NO 36
<211> LENGTH: 57
<212> TYPE: DNA
<213> ORGANISM: Saccharum officinarum

<400> SEQUENCE: 36
ccaaatacct aagtgcactt ttttctgagg ccaaatacct aggttcgaaa gattcgt   57

<210> SEQ ID NO 37
<211> LENGTH: 51
<212> TYPE: DNA
<213> ORGANISM: Saccharum officinarum

<400> SEQUENCE: 37
ccgcctcaaa aggaagtaac acaggaacat gatcatacgg agtagtacta t         51

<210> SEQ ID NO 38
<211> LENGTH: 50
<212> TYPE: DNA
<213> ORGANISM: Saccharum officinarum

<400> SEQUENCE: 38
cttgccggcc gggaccctgc tggcacgatc aagcgactac agtacaatgc         50

<210> SEQ ID NO 39
<211> LENGTH: 59
<212> TYPE: DNA
<213> ORGANISM: Saccharum officinarum

<400> SEQUENCE: 39
caaagaaagc acattaccgc gtatgttacc aacttcctat gttgactatc caaatactg   59

<210> SEQ ID NO 40
<211> LENGTH: 65
<212> TYPE: DNA
<213> ORGANISM: Saccharum officinarum

<400> SEQUENCE: 40
ggattggtct agtacaatct ttattgaaga cgaaagattt atgcatggtg attagttgag   60
cctgt                                                              65

<210> SEQ ID NO 41
<211> LENGTH: 75
<212> TYPE: DNA
<213> ORGANISM: Saccharum officinarum

<400> SEQUENCE: 41
caaatatgac gatggaaata tatagtacta ttaataagac ataacttgca gcatatatta   60
atttcatagg ataag                                                   75

<210> SEQ ID NO 42
<211> LENGTH: 50
<212> TYPE: DNA

<213> ORGANISM: Saccharum officinarum

<400> SEQUENCE: 42
ctagttagag catctccaag cgtactcaga agagtcgccc aatctagcaa                50

<210> SEQ ID NO 43
<211> LENGTH: 50
<212> TYPE: DNA
<213> ORGANISM: Saccharum officinarum

<400> SEQUENCE: 43
cagagaaact gggaacgaaa caggacaata catctgtacg tttggcttgt                50

<210> SEQ ID NO 44
<211> LENGTH: 71
<212> TYPE: DNA
<213> ORGANISM: Saccharum officinarum

<400> SEQUENCE: 44
tccctgtact gtatggtcgc cacaaatgca tattgataga catgtttatg atgtagaatt    60
tgatgtttac a                                                         71

<210> SEQ ID NO 45
<211> LENGTH: 64
<212> TYPE: DNA
<213> ORGANISM: Saccharum officinarum

<400> SEQUENCE: 45
aaatcaataa agaaaggcac gctgaaaata agatggtctg atcgagctcc tgtgtttagt    60
acaa                                                                 64

<210> SEQ ID NO 46
<211> LENGTH: 73
<212> TYPE: DNA
<213> ORGANISM: Saccharum officinarum

<400> SEQUENCE: 46
attccaatga actaagggta agtagagatt attatatata aatcaatgat acacaaactg    60
atcaatcaac taa                                                       73

<210> SEQ ID NO 47
<211> LENGTH: 50
<212> TYPE: DNA
<213> ORGANISM: Saccharum officinarum

<400> SEQUENCE: 47
gccttcttga tctctcagac taagaacata ggcccagagt gaggggaaac                50

<210> SEQ ID NO 48
<211> LENGTH: 70
<212> TYPE: DNA
<213> ORGANISM: Saccharum officinarum

<400> SEQUENCE: 48
cgttcgcttg agcttattag ataaaatcaa tcagcaataa aataatattt ttttctaata    60
aaaatcagca                                                           70

<210> SEQ ID NO 49
<211> LENGTH: 58
<212> TYPE: DNA
<213> ORGANISM: Saccharum officinarum

<400> SEQUENCE: 49
tttatcagct tcggaaatca gcttgagctg acgaagacat caatcttcta catcagat        58

<210> SEQ ID NO 50
<211> LENGTH: 59
<212> TYPE: DNA
<213> ORGANISM: Saccharum officinarum

<400> SEQUENCE: 50
acatgtatgt gcaaaatatc ttgagaccct ctgctttaac atgcatgtcc ttcacatgt        59

<210> SEQ ID NO 51
<211> LENGTH: 50
<212> TYPE: DNA
<213> ORGANISM: Saccharum officinarum

<400> SEQUENCE: 51
cagctctgtc attgccgcca aacacatatg cgccttcatg cccttctccc                  50

<210> SEQ ID NO 52
<211> LENGTH: 50
<212> TYPE: DNA
<213> ORGANISM: Saccharum officinarum

<400> SEQUENCE: 52
agccatcccg cagaggctct tgatgtcctt tgagctgtcc taaaaccact                  50

<210> SEQ ID NO 53
<211> LENGTH: 59
<212> TYPE: DNA
<213> ORGANISM: Saccharum officinarum

<400> SEQUENCE: 53
ctatgtgttg ggcttatatg tgatgcatct ttccttttga attcagggta gtgctgata        59

<210> SEQ ID NO 54
<211> LENGTH: 50
<212> TYPE: DNA
<213> ORGANISM: Saccharum officinarum

<400> SEQUENCE: 54
gtgctgatac gccaccagcc gaaacaaatg gtgatagctc tagcgcacag                  50

<210> SEQ ID NO 55
<211> LENGTH: 50
<212> TYPE: DNA
<213> ORGANISM: Saccharum officinarum

<400> SEQUENCE: 55
aaatcctgaa ggccgaagcc cgtagacatg ttcaccctag caaacaaagg                  50

<210> SEQ ID NO 56
<211> LENGTH: 50
<212> TYPE: DNA
<213> ORGANISM: Saccharum officinarum

<400> SEQUENCE: 56
gcatcggctg gtgctggtag ggataaacct ctgctccgct tgatattttt                  50

<210> SEQ ID NO 57
<211> LENGTH: 71
<212> TYPE: DNA

<213> ORGANISM: Saccharum officinarum

<400> SEQUENCE: 57
ttcgcttgag ttttatcagc agaattaaca gttatatagc ggtgtttttt ctctcacact    60
aaatcagtaa a                                                         71

<210> SEQ ID NO 58
<211> LENGTH: 71
<212> TYPE: DNA
<213> ORGANISM: Saccharum officinarum

<400> SEQUENCE: 58
cttgcctact tcttgcatag atgcttagtt tacattttac ctgaaattta ttaatatcga    60
tcactacaaa t                                                         71

<210> SEQ ID NO 59
<211> LENGTH: 57
<212> TYPE: DNA
<213> ORGANISM: Saccharum officinarum

<400> SEQUENCE: 59
gaacaaggag catccatata tgtatggcac tttgacattg ttggctatgt ctagctt       57

<210> SEQ ID NO 60
<211> LENGTH: 50
<212> TYPE: DNA
<213> ORGANISM: Saccharum officinarum

<400> SEQUENCE: 60
ggaaaagcaa gcagctcgtg tagcaatagt tggcattggc aacagacgcc                50

<210> SEQ ID NO 61
<211> LENGTH: 63
<212> TYPE: DNA
<213> ORGANISM: Saccharum officinarum

<400> SEQUENCE: 61
ggtaaaatta tgcaagttcc cacgaaattt ggcatatgaa agtgcccttt aaaattaagg    60
ttt                                                                  63

<210> SEQ ID NO 62
<211> LENGTH: 73
<212> TYPE: DNA
<213> ORGANISM: Saccharum officinarum

<400> SEQUENCE: 62
gagcttttat ttatgctaac ctgtaacaat aaattgtctt tgagcatggt ttgtttgatg    60
atctcaatga ccg                                                       73

<210> SEQ ID NO 63
<211> LENGTH: 75
<212> TYPE: DNA
<213> ORGANISM: Saccharum officinarum

<400> SEQUENCE: 63
atctacacaa caaatccact gtattagacg attgttatca aatgatcttc cagcaaattg    60
acataatatg acatt                                                     75

<210> SEQ ID NO 64
<211> LENGTH: 66

<212> TYPE: DNA
<213> ORGANISM: Saccharum officinarum

<400> SEQUENCE: 64
agaacagggc catcgttgtt agcgtgcgtg ctgtaagttt gatttaattt aaaaaaaata      60
cgtata                                                                66

<210> SEQ ID NO 65
<211> LENGTH: 58
<212> TYPE: DNA
<213> ORGANISM: Saccharum officinarum

<400> SEQUENCE: 65
acgtacaaat gtttgggatg gcagaggaca tgtagtacag ggttgattct tttcaata        58

<210> SEQ ID NO 66
<211> LENGTH: 50
<212> TYPE: DNA
<213> ORGANISM: Saccharum officinarum

<400> SEQUENCE: 66
gcacctcgct cctccttatc aagtttcgat ttctggattt gctgctcttg                 50

<210> SEQ ID NO 67
<211> LENGTH: 58
<212> TYPE: DNA
<213> ORGANISM: Saccharum officinarum

<400> SEQUENCE: 67
aaggcgaaca aatgattccc ctcagtgacc tgaacgtaat agtaaaatga tacacact        58

<210> SEQ ID NO 68
<211> LENGTH: 50
<212> TYPE: DNA
<213> ORGANISM: Saccharum officinarum

<400> SEQUENCE: 68
tcgcatgtca gggctgacaa atggctaaaa ccagacggaa gatagacgga                 50

<210> SEQ ID NO 69
<211> LENGTH: 70
<212> TYPE: DNA
<213> ORGANISM: Saccharum officinarum

<400> SEQUENCE: 69
aacatcagct tagtctttag aggttatacc tgctgtgcta ttttttttac ttagtgtaca      60
ccattcctga                                                            70

<210> SEQ ID NO 70
<211> LENGTH: 75
<212> TYPE: DNA
<213> ORGANISM: Saccharum officinarum

<400> SEQUENCE: 70
ccttaatcac gcttgtgaaa tatcactcaa accaacaata tcaataccac cattaattat      60
gcttgtgaaa tatgc                                                      75

<210> SEQ ID NO 71
<211> LENGTH: 73
<212> TYPE: DNA
<213> ORGANISM: Saccharum officinarum

<400> SEQUENCE: 71
ttaaagactg aaagaaacaa ttattgaatt aaagaacaac tagatagaga gcactggact      60
gaatggttgc aga                                                          73

<210> SEQ ID NO 72
<211> LENGTH: 70
<212> TYPE: DNA
<213> ORGANISM: Saccharum officinarum

<400> SEQUENCE: 72
atcccatcac aaaggaaaga attgcacaaa caatgacgtg gtacctttaa aagatagaga      60
atggaataga                                                              70

<210> SEQ ID NO 73
<211> LENGTH: 63
<212> TYPE: DNA
<213> ORGANISM: Saccharum officinarum

<400> SEQUENCE: 73
aagcaacaga tgactagaag tacagtgcag gagactccaa cactttacta tattagtaga      60
aga                                                                     63

<210> SEQ ID NO 74
<211> LENGTH: 63
<212> TYPE: DNA
<213> ORGANISM: Saccharum officinarum

<400> SEQUENCE: 74
tcttcagttc atatctatca tctatccgtc gctcgtttca tgagacagat caaataagca      60
gat                                                                     63

<210> SEQ ID NO 75
<211> LENGTH: 70
<212> TYPE: DNA
<213> ORGANISM: Saccharum officinarum

<400> SEQUENCE: 75
ttcgagaatg agcgcattag cacaaggttt aatttcatta atcactttag gtatctagtt      60
aggtgtgtgt                                                              70

<210> SEQ ID NO 76
<211> LENGTH: 50
<212> TYPE: DNA
<213> ORGANISM: Saccharum officinarum

<400> SEQUENCE: 76
cgcccaccaa tgcattaccc aatggggtac ccgatgccgc cccattcgca                  50

<210> SEQ ID NO 77
<211> LENGTH: 50
<212> TYPE: DNA
<213> ORGANISM: Saccharum officinarum

<400> SEQUENCE: 77
gtgcagggta cccgtcaatg ggctacggct atggccgccc accaatgcat                  50

<210> SEQ ID NO 78
<211> LENGTH: 74
<212> TYPE: DNA
<213> ORGANISM: Saccharum officinarum

```
<400> SEQUENCE: 78
aagataaatt tacaagcaaa attagaatgt caaataccac aaatattgag agctgtgcct      60
gacaattgag gaga                                                        74

<210> SEQ ID NO 79
<211> LENGTH: 50
<212> TYPE: DNA
<213> ORGANISM: Saccharum officinarum

<400> SEQUENCE: 79
agctgtgcct gacaattgag agtgaacaga gtacatttca tactgcccag                 50

<210> SEQ ID NO 80
<211> LENGTH: 50
<212> TYPE: DNA
<213> ORGANISM: Saccharum officinarum

<400> SEQUENCE: 80
tccggagatt acaacgtctt cagtgacgag aacccgaaca gctgctcggt                 50

<210> SEQ ID NO 81
<211> LENGTH: 58
<212> TYPE: DNA
<213> ORGANISM: Saccharum officinarum

<400> SEQUENCE: 81 ccoctgacac gatatttatt tgccagaatt tatgaattac agccgcattt cgttgtgt        58

<210> SEQ ID NO 82
<211> LENGTH: 68
<212> TYPE: DNA
<213> ORGANISM: Saccharum officinarum

<400> SEQUENCE: 82
ttggcaatca tcgactaatt aggtgtaaaa gattcgtctt gttatttttct accaaattat     60 gaaattta                                                               68

<210> SEQ ID NO 83
<211> LENGTH: 75
<212> TYPE: DNA
<213> ORGANISM: Saccharum officinarum

<400> SEQUENCE: 83
tatagggcca gataaaccat gataatcata ggatatttgc agaaatctta aatttctgag      60
attgccaaca gaaga                                                       75

<210> SEQ ID NO 84
<211> LENGTH: 59
<212> TYPE: DNA
<213> ORGANISM: Saccharum officinarum

<400> SEQUENCE: 84
tatggatctt ccagttgatt actgttcttt cgctccgctt tttgcttttt tactcgtga      59

<210> SEQ ID NO 85
<211> LENGTH: 50
<212> TYPE: DNA
<213> ORGANISM: Saccharum officinarum

<400> SEQUENCE: 85
```

```
tactcgtgag ggtccatcta tgacctatcc tgtgttcttt actagcgaaa          50

<210> SEQ ID NO 86
<211> LENGTH: 18
<212> TYPE: DNA
<213> ORGANISM: Artificial Sequence
<220> FEATURE:
<223> OTHER INFORMATION: Synthetic DNA

<400> SEQUENCE: 86
cacgatggat ccagtgca                                              18

<210> SEQ ID NO 87
<211> LENGTH: 16
<212> TYPE: DNA
<213> ORGANISM: Artificial Sequence
<220> FEATURE:
<223> OTHER INFORMATION: Synthetic DNA

<400> SEQUENCE: 87
ctggatccat cgtgca                                                16

<210> SEQ ID NO 88
<211> LENGTH: 16
<212> TYPE: DNA
<213> ORGANISM: Artificial Sequence
<220> FEATURE:
<223> OTHER INFORMATION: Synthetic DNA

<400> SEQUENCE: 88
gatggatcca gtgcag                                                16
```

MARKER ASSOCIATED WITH RESISTANCE TO SMUT IN PLANT BELONGING TO GENUS *SACCHARUM*, AND USE THEREOF

CROSS-REFERENCE TO RELATED APPLICATIONS

This application is a Divisional of U.S. application Ser. No. 14/113,539 filed Oct. 23, 2013, which is a National Stage of International Application No. PCT/JP2012/060671, filed Apr. 20, 2012, which claims priority to Japanese Patent Application No. 2011-101050, filed Apr. 28, 2011, and to Japanese Patent Application No. 2012-094995, filed Apr. 18, 2012, the contents of all of which are incorporated herein by reference in their entirety.

TECHNICAL FIELD

The present invention relates to a marker associated with resistance to smut whereby a sugarcane line resistant to smut can be selected, and a method for use thereof.

BACKGROUND ART

Sugarcane has been cultivated as a raw material for sugar, liquor, and the like for edible use. In addition, sugarcane has been used as, for example, a raw material for biofuel in a variety of industrial fields. Under such circumstances, there is a need to develop novel sugarcane varieties having desirable characteristics (e.g., sugar content, enhanced vegetative capacity, sprouting capacity, disease resistance, insect resistance, cold resistance, an increase in leaf blade length, an increase in leaf area, and an increase in stalk length).

In general, the following three ways may be used for identification of a plant variety/line: "characteristics comparison" for comparison of characteristics data, "comparison during cultivation" for comparison of plants cultivated under the same conditions, and "DNA assay" for DNA analysis. There are many problems in line identification with characteristics comparison or comparison during cultivation, including reduction of precision due to differences in cultivation conditions, lengthy duration of field research that requires a number of steps, and the like. In particular, since sugarcane plants are much larger than other graminaceous crops such as rice and maize, it has been difficult to conduct line identification based on field research.

In addition, in order to identify a variety resistant to a certain disease, an inoculation test is carried out using a causative microorganism of a disease after long-term cultivation of sugarcane, and then disease resistance data are collected by observing lesions and the like. However, transmission of the causative microorganism to an external environment must be securely prevented when the test is carried out, and thus it is necessary to provide, for example, facilities such as a large-scale special-purpose greenhouse, a special-purpose field or isolation facility from an external environment. Further, for creation of a novel sugarcane variety, first, tens of thousands of hybrids are created via crossing, followed by seedling selection and stepwise selection of desirable excellent lines. Eventually, 2 or 3 types of novel varieties having desired characteristics can be obtained. As described above, for creation of a novel sugarcane variety, it is necessary to cultivate and evaluate an enormous number of lines, and it is also necessary to prepare the above large-scale greenhouse or field and undertake highly time-consuming efforts.

Therefore, it has been required to develop a method for identifying a sugarcane line having disease resistance with the use of markers present in the sugarcane genome. In particular, upon creation of a novel sugarcane variety, if excellent markers could be used to examine a variety of characteristics, the above problems particular to sugarcane would be resolved, and the markers would be able to serve as very effective tools. However, since sugarcane plants have a large number of chromosomes (approximately 100 to 130) due to higher polyploidy, the development of marker technology has been slow. In the case of sugarcane, although the USDA reported genotyping with the use of SSR markers (Non-Patent Literature 1), the precision of genotyping is low because of the small numbers of markers and polymorphisms in each marker. In addition, the above genotyping is available only for American/Australian varieties, and therefore it cannot be used for identification of the major varieties cultivated in Japan, Taiwan, India, and other countries or lines that serve as useful genetic resources.

In addition, Non-Patent Literature 2 suggests the possibility that a sugarcane genetic map can be created by increasing the number of markers, comparing individual markers in terms of a characteristic relationship, and verifying the results. However, in Non-Patent Literature 2, an insufficient number of markers are disclosed and markers linked to desired characteristics have not been found.

Meanwhile, as a marker associated with disease resistance, a marker associated with black root rot resistance in sugar beet disclosed in Patent Literature 1 is known. In addition, a technique of selecting a *Zea mays* variety using a maker linked to a desired trait is disclosed in Patent Literature 2.

The level of infectiousness of the causative microorganism of sugarcane smut is high, and therefore the onset of smut quickly results in the infection of the entire field. Crops of sugarcane affected with smut cannot be used as raw material for sugar production, and even they die. Therefore, the development of smut will cause a significant decline in yield within the following year or later. Damage due to smut has been reported in more than 28 countries, including Brazil, the U.S., Australia, China, and Indonesia. Smut can be prevented by sterilization treatment prior to planting; however, preventive effects are limited to the period of early growth. Thus, cultivation of a sugarcane variety imparted with smut resistance has been awaited.

CITATION LIST

Non-Patent Literature

Non-Patent Literature 1: Maydica 48(2003) 319-329 "Molecular genotyping of sugarcane clones with microsatellite DNA markers"

Non-Patent Literature 2: Nathalie Piperidis et al., Molecular Breeding, 2008, Vol. 21, 233-247

Patent Literature

Patent Literature 1: WO 2007/125958

Patent Literature 2: JP Patent Publication (Kokai) No. 2010-516236 A

SUMMARY OF INVENTION

Technical Problem

In view of the above, an object of the present invention is to provide a marker associated with resistance to smut, which is a quantitative trait of sugarcane.

Solution to Problem

In order to achieve the object, the present inventors conducted intensive studies. The present inventors prepared many sugarcane plant markers and carried out linkage analysis of quantitative traits along with such markers for hybrid progeny lines. Accordingly, the present inventors found markers linked to quantitative traits such as smut resistance. This has led to the completion of the present invention.

The present invention encompasses the following.

(1) A marker associated with resistance to sugarcane smut, which consists of a continuous nucleic acid region existing in a region sandwiched between the nucleotide sequence shown in SEQ ID NO: 1 and the nucleotide sequence shown in SEQ ID NO: 14, a region sandwiched between the nucleotide sequence shown in SEQ ID NO: 15 and the nucleotide sequence shown in SEQ ID NO: 22, a region sandwiched between the nucleotide sequence shown in SEQ ID NO: 23 and the nucleotide sequence shown in SEQ ID NO: 32, a region sandwiched between the nucleotide sequence shown in SEQ ID NO: 33 and the nucleotide sequence shown in SEQ ID NO: 51, a region sandwiched between the nucleotide sequence shown in SEQ ID NO: 52 and the nucleotide sequence shown in SEQ ID NO: 62, a region sandwiched between the nucleotide sequence shown in SEQ ID NO: 63 and the nucleotide sequence shown in SEQ ID NO: 72, or a region sandwiched between the nucleotide sequence shown in SEQ ID NO: 73 and the nucleotide sequence shown in SEQ ID NO: 85 of a sugarcane chromosome.

(2) The marker associated with resistance to sugarcane smut according to (1), wherein the continuous nucleic acid region comprises any nucleotide sequence selected from the group consisting of the nucleotide sequences shown in SEQ ID NOS: 1 to 85 or a part of the nucleotide sequence.

(3) The marker associated with resistance to sugarcane smut according to (1), wherein the continuous nucleic acid region is located at a position in a region sandwiched between the nucleotide sequence shown in SEQ ID NO: 5 and the nucleotide sequence shown in SEQ ID NO: 9, a region sandwiched between the nucleotide sequence shown in SEQ ID NO: 18 and the nucleotide sequence shown in SEQ ID NO: 22, a region sandwiched between the nucleotide sequence shown in SEQ ID NO: 25 and the nucleotide sequence shown in SEQ ID NO: 32, a region sandwiched between the nucleotide sequence shown in SEQ ID NO: 33 and the nucleotide sequence shown in SEQ ID NO: 42, a region sandwiched between the nucleotide sequence shown in SEQ ID NO: 57 and the nucleotide sequence shown in SEQ ID NO: 59, a region sandwiched between the nucleotide sequence shown in SEQ ID NO: 64 and the nucleotide sequence shown in SEQ ID NO: 66, or a region sandwiched between the nucleotide sequence shown in SEQ ID NO: 72 and the nucleotide sequence shown in SEQ ID NO: 80 of a sugarcane chromosome.

(4) A method for producing a sugarcane line having improved smut resistance comprising: a step of extracting a chromosome of a progeny plant obtained from parent plants, at least one of which is a sugarcane plant, and/or a chromosome of a parent sugarcane plant; and a step of determining the presence or absence of the marker associated with resistance to sugarcane smut according to any one of (1) to (3) in the obtained chromosome.

(5) The method for producing a sugarcane line according to (4), wherein a DNA chip comprising a probe corresponding to the marker associated with resistance to sugarcane smut is used in the determination step.

(6) The method for producing a sugarcane line according to (4), wherein the progeny plant is in the form of seeds or a young seedling and the chromosome is extracted from the seeds or the young seedling.

This specification includes part or all of the contents as disclosed in the specification and/or drawings of Japanese Patent Application Nos. 2011-101050 and 2012-94995, which are priority documents of the present application.

Advantageous Effects of Invention

According to the present invention, a novel marker associated with resistance to sugarcane smut linked to a sugarcane quantitative trait such as smut resistance can be provided. With the use of the marker associated with resistance to sugarcane smut of the present invention, smut resistance of a line obtained by crossing sugarcane lines can be tested. Thus, a sugarcane line characterized by improved smut resistance can be identified at a very low cost.

DESCRIPTION OF EMBODIMENTS

Figure 1:
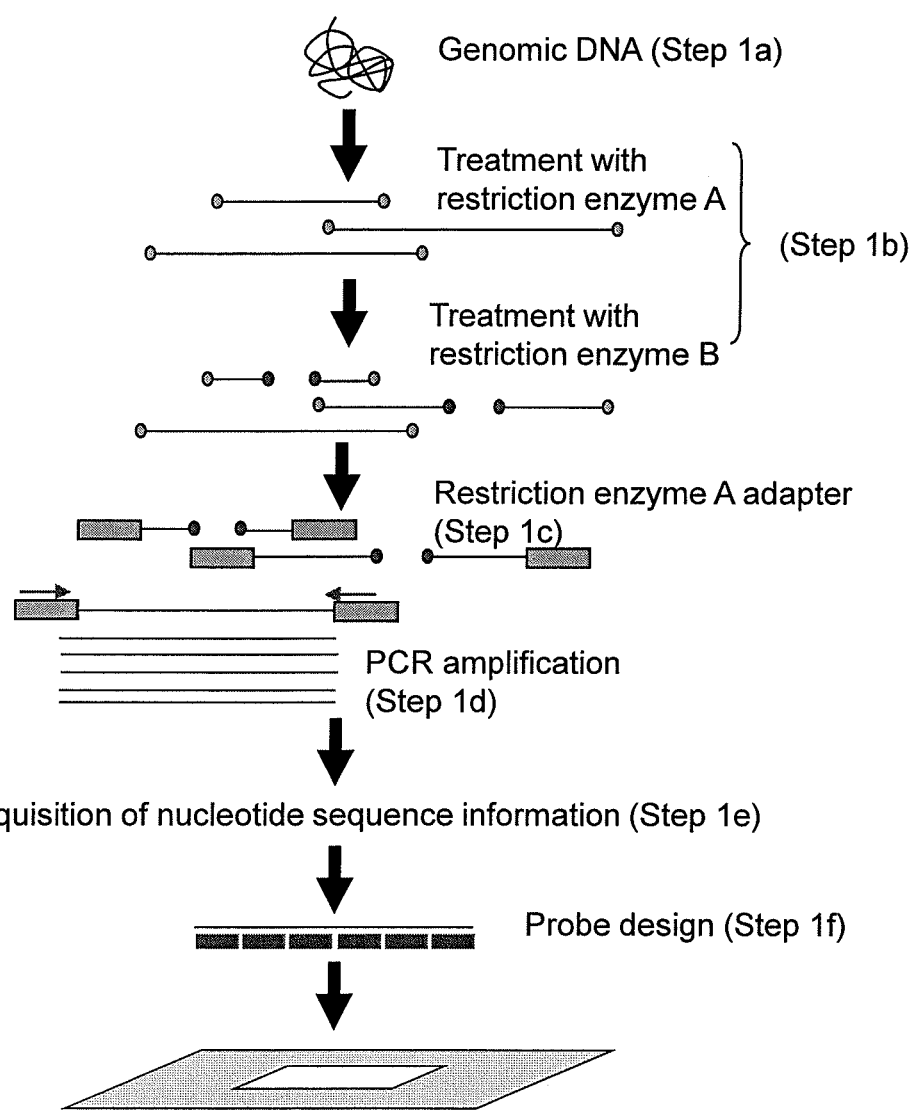
FIG. 1 schematically shows the process of production of a DNA microarray used for acquisition of sugarcane chromosome markers.

The marker associated with resistance to sugarcane smut and the method for using the same according to the present invention are described below. In particular, a method for producing a sugarcane line using a marker associated with resistance to sugarcane smut is described.

<Markers Associated with Resistance to Sugarcane Smut>

The marker associated with resistance to sugarcane smut of the present invention corresponds to a specific region present on a sugarcane chromosome and is linked to a causative gene (or a group of causative genes) for a trait characterized by smut resistance. Thus, it can be used to identify a trait characterized by smut resistance. Specifically, it is possible to determine that a progeny line obtained using a known sugarcane line is a line having a trait characterized by the improvement of smut resistance by confirming the presence or absence of the marker associated with resistance to sugarcane smut in such progeny line. In the present invention, the term "smut" refers to a disease characterized by lesion formation due to infection with a microorganism of the genus *Ustilago*. One example of a microorganism of the genus *Ustilago* is *Ustilago scitaminea*.

In addition, the term "marker associated with resistance to sugarcane smut" refers to both a marker linked to a trait characterized by the improvement of smut resistance and a marker linked to a trait characterized by the reduction of smut resistance. For example, if the presence of the former marker in a certain sugarcane variety is confirmed, it is possible to determine that the variety has improved smut resistance. Further, if the presence of the former marker and the absence of the latter marker in a certain sugarcane variety are confirmed, it is possible to determine that the variety has improved smut resistance with high accuracy. It is also possible to determine that a certain sugarcane variety has improved smut resistance by confirming only the absence of the latter marker.

The term "sugarcane" used herein refers to a plant belonging to the genus *Saccharum* of the family Poaceae. In addition, the term "sugarcane" includes so-called noble cane (scientific name: *Saccharum officinarum*) and wild cane (scientific name: *Saccharum spontaneum*), *Saccharum barberi*, *Saccharum sinense*, and the earlier species of *Saccharum officinarum* (*Saccharum robustum*). The term "known sugarcane variety/line" is not particularly limited. It includes any variety/line available in Japan and any variety/line available outside Japan. Examples of sugarcane varieties cultivated in Japan include, but are not limited to, Ni1, NiN2, NiF3, NiF4, NiF5, Ni6, NiN7, NiF8, Ni9, NiTn10, Ni11, Ni12, Ni14, Ni15, Ni16, Ni17, NiTn19, NiTn20, Ni22, and Ni23. Examples of main sugarcane varieties used in Japan described herein include, but are not limited to, NiF8, Ni9, NiTn10, and Ni15. In addition, examples of main sugarcane varieties that have been introduced into Japan include, but are not limited to, F177, Nco310, and F172.

In addition, a progeny line may be a line obtained by crossing a mother plant and a father plant of the same species, each of which is a sugarcane variety/line, or it may be a hybrid line obtained from parent plants when one thereof is a sugarcane variety/line and the other is a closely related variety/line (*Erianthus arundinaceus*). In addition, a progeny line may be obtained by so-called backcrossing.

The marker associated with resistance to sugarcane smut of the present invention has been newly identified by QTL (Quantitative Trait Loci) analysis using a genetic linkage map containing 3004 markers and 4569 markers originally obtained from sugarcane chromosomes, and sugarcane smut resistance data. In addition, many genes are presumably associated with sugarcane smut resistance, which is a quantitative trait characterized by a continuous distribution of sugarcane smut resistance. That is, sugarcane smut resistance is evaluated based on the incidence of smut characterized by such continuous distribution. For QTL analysis, the QTL Cartographer gene analysis software (Wang S., C. J. Basten, and Z.-B. Zeng (2010); Windows QTL Cartographer 2.5. Department of Statistics, North Carolina State University, Raleigh, N.C.) is used, and the analysis is carried out by the composite interval mapping (CIM) method.

Specifically, seven relevant regions included in the above genetic linkage map with LOD scores equivalent to or exceeding a given threshold (e.g., 2.5) have been found by QTL analysis described above. That is, the following 7 regions have been specified: an approximately 18.7-cM (centimorgan) region including the relevant region, an approximately 39.2-cM region including the relevant region, an approximately 19.2-cM region including the relevant region, an approximately 32.0-cM region including the relevant region, an approximately 39.5-cM region including the relevant region, an approximately 53.4-cM region including the relevant region, and an approximately 38.0-cM region including the relevant region. The term "morgan (M)" used herein refers to a unit representing the relative distance between genes on a chromosome, and it is expressed by the percentage of the crossover rate. In a case of a sugarcane chromosome, 1 cM corresponds to approximately 2000 kb. In addition, it is suggested that a causative gene (or a group of causative genes) for a trait that causes the improvement of smut resistance could be present at the peak positions or in the vicinity thereof.

The 18.7-cM region is a region that comprises 14 types of markers listed in table 1 below in the order shown in table 1 and is linked to a trait characterized by the reduction of smut resistance.

TABLE 1

| Linkage group | Marker name | Nucleotide sequence information | Signal threshold | SEQ ID NO: |
|---|---|---|---|---|
| NiF8_5 | N827337 | CCTCGTCATGC ACCCGTGCCTC TTCTTCCTCTT GCTGTTGCTCC TCCTCC | 1,000 | SEQ ID NO: 1 |
| | N802879 | GGAATTGTTGT AGATTTGTTTT GTGATGGAAAG ATCATACCTCA GCTACAAGAAG TAAATATCCTT TTCCA | 1,000 | SEQ ID NO: 2 |

TABLE 1-continued

| Linkage group | Marker name | Nucleotide sequence information | Signal threshold | SEQ ID NO: |
|---|---|---|---|---|
| | N804818 | GGCATTAGAAGAAAGGTGGAAGAATAAGGTTTGAGCCCTTATTTATTTGCTTTGGTGATGGAT | 1,000 | SEQ ID NO: 3 |
| | N816296 | CCATTCTACTTCTACCAACCATAAAACAGGAGGAGCATGCATGCACATGC | 1,000 | SEQ ID NO: 4 |
| | N804607 | ATTGCTTGCTCGCTGCAACTTGGGCCATGTTTAGTTCCTCGAATTTGAGT | 1,000 | SEQ ID NO: 5 |
| | N802870 | AGTGAAGAGATTGGATTTCTAGGGTTACTTTATAAAGTGTCAACACCTTAGATCTGTTTTTTAGT | 1,500 | SEQ ID NO: 6 |
| | N813249 | GGCCGGCACGAGCATCAGGGTCAAGACTCAAGAGCTCAAGTGCTTGCTTT | 1,500 | SEQ ID NO: 7 |
| | N813609 | TACTTTGTCTCGTTCCAGTAGTCCATCAAGCAAGCCTCGTACACAAGTCC | 1,000 | SEQ ID NO: 8 |
| | N815502 | TGCACTGGGATACCAGTTGAGTTGATTGCACAACTTGCGCTACACCATG | 1,000 | SEQ ID NO: 9 |
| | N815101 | GCCGCCTGATGGAAACGGTCGTCGCATCCAAAGACGCACATGGTTTAGCA | 1,000 | SEQ ID NO: 10 |
| | N823481 | AGTACCTGTTCTGCTGCACTACATAACAGTACTTTTCAGTGAACGAACAGTGTTTTC | 1,000 | SEQ ID NO: 11 |
| | N801028 | AGCGGATAGCGCTAGCATGTCATTCTCTCCCCTCGCTAGCACGTTATTCC | 1,500 | SEQ ID NO: 12 |
| | N810798 | GTTGCGGCGTGTGTTGATGATGTAAAGAATACTCGTCCGTGAGAAATTATCA | 1,500 | SEQ ID NO: 13 |
| | N821515 | ACGTGACGACGACGACGATGCAGCTGGGGCTTGGCGTGGAATGGTTGTCG | 1,000 | SEQ ID NO: 14 |

The 39.2-cM region is a region that comprises 8 types of markers listed in table 2 below in the order shown in table 2 and is linked to a trait characterized by the improvement of smut resistance.

TABLE 2

| Linkage group | Marker name | Nucleotide sequence information | Signal threshold | SEQ ID NO: |
|---|---|---|---|---|
| NiF8_17 | N826561 | GGCCTTGTTTAAATGTCACCTAAATTCTAAATTTTACACTCTTTTCATAACATCGAATCTTAAAA | 1,000 | SEQ ID NO: 15 |
| | N827136 | AAACTGAGGGATTACTTTCCAATTGAAATGTCATCCACCACAAACACAAAAGGCATACTCA | 1,500 | SEQ ID NO: 16 |
| | N826325 | ACACTACACTGTGTAGGCAATGAGCAGCTCTGTTGCACAGCAAAGCCAAA | 1,000 | SEQ ID NO: 17 |
| | N803928 | GGATGTGAAGTATGTATGTGTTTTCAGATGGACCAAGGAAGCTGCATGGG | 1,000 | SEQ ID NO: 18 |
| | N822568 | TACGGTGGTACAAAGCTTAGATCAATGATCAAGCTACAAAACACACAAAGATAGTCAGTAGAAAAAGT | 1,000 | SEQ ID NO: 19 |
| | N829026 | GACGACGAGGTGGGCAGCGCCAGTGCGCTACTACCTTCTTTCTTGCAACT | 1,000 | SEQ ID NO: 20 |
| | N815300 | GTATGGTTATGTTGGTACTAAAGGTTTCTGACTATTGTATTGTATTGTTGTGTTATAATGGGTTCAATG | 1,000 | SEQ ID NO: 21 |
| | N826906 | GGCTGCAATACCTGTTCCTCATCTCATCTATTCGTGCAAAGTTGCTGGTC | 1,000 | SEQ ID NO: 22 |

The 19.2-cM region is a region that comprises 10 types of markers listed in table 3 below in the order shown in table 3 and is linked to a trait characterized by the reduction of smut resistance.

TABLE 3

| Linkage group | Marker name | Nucleotide sequence information | Signal threshold | SEQ ID NO: |
|---|---|---|---|---|
| NiF8_40 | N816552 | TCGGGTTGGAGGCAAGGAAGAAAGGAGCTAGATTGCTCGGCTGCTGGTGC | 1,500 | SEQ ID NO: 23 |
| | N827448 | ACAGTAGTGCAACTGCGACGACGATGTGTGGGTATATGTTCCATAGCTTG | 1,000 | SEQ ID NO: 24 |
| | N829378 | TTTTGATTGGCCTTGCAGATGTTGCAGCGATGGCACTCGTGGCAAACAGA | 900 | SEQ ID NO: 25 |

TABLE 3-continued

| Linkage group | Marker name | Nucleotide sequence information | Signal threshold | SEQ ID NO: |
|---|---|---|---|---|
| | N829404 | AACCATGCTGAAAACGTCTTCCGTTTACAGTTTATGGTATATCCGCTTAAAACTAACTCGATC | 1,000 | SEQ ID NO: 26 |
| | N828725 | AATCTAAATGACTAATGAGACCGTGAGAGCTGCTTAGCTTAATGGTGCATCCCTTTTTAAACT | 1,000 | SEQ ID NO: 27 |
| | N812680 | AAGAACACTGCTAAGGATGGTCACAATTTGGAAACTGAAGTTTTATCTCTGGTTCGGT | 1,500 | SEQ ID NO: 28 |
| | N811688 | AAGCTGCATCTGATTCTCATCCAAACCTGCTCTGCTCATTATCATTACTTCGT | 1,000 | SEQ ID NO: 29 |
| | N819703 | CCAACCAACAGCAAGAACACCAAGACGCACATAATGAGGCCCATGAAGTA | 1,500 | SEQ ID NO: 30 |
| | N815648 | TTTACACCAGTGAACTGACAAAAAATCGAAGTGGTGCGGTACATAAGAACATTTACATCCAACT | 1,000 | SEQ ID NO: 31 |
| | N821999 | GACCAATCTAGGAAAAACAATTGCACAAATGACTACATTTATTATGGCAAATCAATTTTCTTCAGTCATTGTA | 1,000 | SEQ ID NO: 32 |

The 32.0-cM region is a region that comprises 19 types of markers listed in table 4 below in the order shown in table 4 and is linked to a trait characterized by the improvement of smut resistance.

TABLE 4

| Linkage group | Marker name | Nucleotide sequence information | Signal threshold | SEQ ID NO: |
|---|---|---|---|---|
| Ni9_1 | N915070 | ATAGTCTACCTATACTGGTGCCACAAGTCAACAAGTGATGGCAATACCCATTCAAATT | 1,000 | SEQ ID NO: 33 |
| | N915209 | TGGCAATACCCATTCAAATTGCGTCAAATGTGAATAAATGGAGGTAGATGACTAACACCTTTGTTTCAAA | 1,000 | SEQ ID NO: 34 |
| | N916186 | CTGCAATACAATGCGGTGGAAGCGGATTGGTGGAAGGCATGCATGCATCA | 1,000 | SEQ ID NO: 35 |
| | N902342 | CCAAATACCTAAGTGCACTTTTTTCTGAGGCCAAATACCTAGGTTCGAAAGATTCGT | 900 | SEQ ID NO: 36 |
| | N919949 | CCGCCTCAAAAGGAAGTAACACAGGAACATGATCATACGGAGTAGTACTAT | 1,000 | SEQ ID NO: 37 |
| | N920597 | CTTGCCGGCCGGGACCCTGCTGGCACGATCAAGCGACTACAGTACAATGC | 1,500 | SEQ ID NO: 38 |
| | N916081 | CAAAGAAAGCACATTACCGCGTATGTTACCAACTTCCTATGTTGACTATCCAAATACTG | 4,000 | SEQ ID NO: 39 |
| | N902047 | GGATTGGTCTAGTACAATCTTTATTGAAGACGAAAGATTTATGCATGGTGATTAGTTGAGCCTGT | 1,500 | SEQ ID NO: 40 |
| | N916874 | CAAATATGACGATGGAAATATATAGTACTATTAATAAGACATAACTTGCAGCATATATTAATTTCATAGGATAAG | 1,000 | SEQ ID NO: 41 |
| | N918161 | CTAGTTAGAGCATCTCCAAGCGTACTCAGAAGAGTCGCCCAATCTAGCAA | 1,000 | SEQ ID NO: 42 |
| | N918536 | CAGAGAAACTGGGAACGAAACAGGACAATACATCTGTACGTTTGGCTTGT | 900 | SEQ ID NO: 43 |
| | N901676 | TCCCTGTACTGTATGGTCGCCACAAATGCATATTGATAGACATGTTTATGATGTAGAATTTGATGTTTACA | 1,000 | SEQ ID NO: 44 |
| | N919743 | AAATCAATAAAGAAAGGCACGCTGAAAATAAGATGGTCTGATCGAGCTCCTGTGTTTAGTACAA | 1,000 | SEQ ID NO: 45 |
| | N901176 | ATTCCAATGAACTAAGGGTAAGTAGAGATTATTATATATAAATCAATGATACACAAACTGATCAATCAACTAA | 1,500 | SEQ ID NO: 46 |
| | N916035 | GCCTTCTTGATCTCTCAGACTAAGAACATAGGCCCAGAGTGAGGGGAAAC | 1,500 | SEQ ID NO: 47 |
| | N921010 | CGTTCGCTTGAGCTTATTAGATAAAATCAATCAGCAATAAAATAATATTTTTTTCTAATAAAAATCAGCA | 1,500 | SEQ ID NO: 48 |
| | N915635 | TTTATCAGCTTCGGAAATCAGC | 4,000 | SEQ ID NO: 49 |

TABLE 4-continued

| Linkage group | Marker name | Nucleotide sequence information | Signal threshold | SEQ ID NO: |
|---|---|---|---|---|
| | | TTGAGCTGACG AAGACATCAAT CTTCTACATCA GAT | | |
| | N901348 | ACATGTATGTG CAAAATATCTT GAGACCCTCTG CTTTAACATGC ATGTCCTTCAC ATGT | 1,500 | SEQ ID NO: 50 |
| | N920207 | CAGCTCTGTCA TTGCCGCCAAA CACATATGCGC CTTCATGCCCT TCTCCC | 1,500 | SEQ ID NO: 51 |

The 39.5-cM region is a region that comprises 11 types of markers listed in table 5 below in the order shown in table 5 and is linked to a trait characterized by the reduction of smut resistance.

TABLE 5

| Linkage group | Marker name | Nucleotide sequence information | Signal threshold | SEQ ID NO: |
|---|---|---|---|---|
| Ni9_13 | N914284 | AGCCATCCCGC AGAGGCTCTTG ATGTCCTTTGA GCTGTCCTAAA ACCACT | 1,000 | SEQ ID NO: 52 |
| | N901453 | CTATGTGTTGG GCTTATATGTG ATGCATCTTTC CTTTTGAATTC AGGGTAGTGCT GATA | 1,000 | SEQ ID NO: 53 |
| | N900044 | GTGCTGATACG CCACCAGCCGA AACAAATGGTG ATAGCTCTAGC GCACAG | 1,000 | SEQ ID NO: 54 |
| | N919839 | AAATCCTGAAG GCCGAAGCCCG TAGACATGTTC ACCCTAGCAAA CAAAGG | 1,500 | SEQ ID NO: 55 |
| | N901567 | GCATCGGCTGG TGCTGGTAGGG ATAAACCTCTG CTCCGCTTGAT ATTTTT | 1,500 | SEQ ID NO: 56 |
| | N911103 | TTCGCTTGAGT TTTATCAGCAG AATTAACAGTT ATATAGCGGTG TTTTTTCTCTC ACACTAAATCA GTAAA | 800 | SEQ ID NO: 57 |
| | N918508 | CTTGCCTACTT CTTGCATAGAT GCTTAGTTTAC ATTTTACCTGA AATTTATTAAT ATCGATCACTA CAAAT | 1,500 | SEQ ID NO: 58 |
| | N918344 | GAACAAGGAGC ATCCATATATG TATGGCACTTT GACATTGTTGG CTATGTCTAGC TT | 1,000 | SEQ ID NO: 59 |

TABLE 5-continued

| Linkage group | Marker name | Nucleotide sequence information | Signal threshold | SEQ ID NO: |
|---|---|---|---|---|
| | N919696 | GGAAAAGCAAG CAGCTCGTGTA GCAATAGTTGG CATTGGCAACA GACGCC | 1,000 | SEQ ID NO: 60 |
| | N916172 | GGTAAAATTAT GCAAGTTCCCA CGAAATTTGGC ATATGAAAGTG CCCTTAAAAAT TAAGGTTT | 1,500 | SEQ ID NO: 61 |
| | N916129 | GAGCTTTTATT TATGCTAACCT GTAACAATAAA TTGTCTTTGAG CATGGTTTGTT TGATGATCTCA ATGACCG | 1,500 | SEQ ID NO: 62 |

The 53.4-cM region is a region that comprises 10 types of markers listed in table 6 below in the order shown in table 6 and is linked to a trait characterized by the reduction of smut resistance.

TABLE 6

| Linkage group | Marker name | Nucleotide sequence information | Signal threshold | SEQ ID NO: |
|---|---|---|---|---|
| Ni9_14_1 | N901178 | ATCTACACAAC AAATCCACTGT ATTAGACGATT GTTATCAAATG ATCTTCCAGCA AATTGACATAA TATGACATT | 1,000 | SEQ ID NO: 63 |
| | N918761 | AGAACAGGGCC ATCGTTGTTAG CGTGCGTGCTG TAAGTTTGATT TAATTTAAAAA AAATACGTATA | 1,500 | SEQ ID NO: 64 |
| | N913735 | ACGTACAAATG TTTGGGATGGC AGAGGACATGT AGTACAGGGTT GATTCTTTTCA ATA | 1,000 | SEQ ID NO: 65 |
| | N900663 | GCACCTCGCTC CTCCTTATCAA GTTTCGATTTC TGGATTTGCTG CTCTTG | 1,000 | SEQ ID NO: 66 |
| | N918363 | AAGGCGAACAA ATGATTCCCCT CAGTGACCTGA ACGTAATAGTA AAATGATACAC ACT | 1,000 | SEQ ID NO: 67 |
| | N918213 | TCGCATGTCAG GGCTGACAAAT GGCTAAAACCA GACGGAAGATA GACGGA | 1,000 | SEQ ID NO: 68 |
| | N900568 | AACATCAGCTT AGTCTTTAGAG GTTATACCTGC TGTGCTATTTT TTTTACTTAGT GTACACCATTC CTGA | 1,000 | SEQ ID NO: 69 |
| | N912523 | CCTTAATCACG CTTGTGAAATA | 1,500 | SEQ ID NO: 70 |

TABLE 6-continued

| Linkage group | Marker name | Nucleotide sequence information | Signal threshold | SEQ ID NO: |
|---|---|---|---|---|
| | N900344 | TCACTCAAACC AACAATATCAA TACCACCATTA ATTATGCTTGT GAAATATGC TTAAAGACTGA AAGAAACAATT ATTGAATTAAA GAACAACTAGA TAGAGAGCACT GGACTGAATGG TTGCAGA | 1,500 | SEQ ID NO: 71 |
| | N900802 | ATCCCATCACA AAGGAAAGAAT TGCACAAACAA TGACGTGGTAC CTTTAAAGAT AGAGAATGGAA TAGA | 1,500 | SEQ ID NO: 72 |

The 38.0-cM region is a region that comprises 13 types of markers listed in table 7 below in the order shown in table 7 and is linked to a trait characterized by the improvement of smut resistance.

TABLE 7

| Linkage group | Marker name | Nucleotide sequence information | Signal threshold | SEQ ID NO: |
|---|---|---|---|---|
| Ni9_14_2 | N901524 | AAGCAACAGAT GACTAGAAGTA CAGTGCAGGAG ACTCCAACACT TTACTATATTA GTAGAAGA | 1,000 | SEQ ID NO: 73 |
| | N901163 | TCTTCAGTTCA TATCTATCATC TATCCGTCGCT CGTTTCATGAG ACAGATCAAAT AAGCAGAT | 1,000 | SEQ ID NO: 74 |
| | N911063 | TTCGAGAATGA GCGCATTAGCA CAAGGTTTAAT TTCATTAATCA CTTTAGGTATC TAGTTAGGTGT GTGT | 1,000 | SEQ ID NO: 75 |
| | N914692 | CGCCCACCAAT GCATTACCCAA TGGGGTACCCG ATGCCGCCCCA TTCGCA | 1,500 | SEQ ID NO: 76 |
| | N911405 | GTGCAGGGTAC CCGTCAATGGG CTACGGCTATG GCCGCCCACCA ATGCAT | 1,000 | SEQ ID NO: 77 |
| | N913383 | AAGATAAATTT ACAAGCAAAAT TAGAATGTCAA ATACCACAAAT ATTGAGAGCTG TGCCTGACAAT TGAGGAGA | 1,000 | SEQ ID NO: 78 |
| | N914112 | AGCTGTGCCTG ACAATTGAGAG TGAACAGAGTA CATTTCATACT GCCCAG | 1,000 | SEQ ID NO: 79 |
| | N915180 | TCCGGAGATTA CAACGTCTTCA | 1,000 | SEQ ID NO: 80 |

TABLE 7-continued

| Linkage group | Marker name | Nucleotide sequence information | Signal threshold | SEQ ID NO: |
|---|---|---|---|---|
| | N901160 | GTGACGAGAAC CCGAACAGCTG CTCGGT CCCCTGACACG ATATTTATTTG CCAGAATTTAT GAATTACAGCC GCATTTCGTTG TGT | 1,500 | SEQ ID NO: 81 |
| | N916293 | TTGGCAATCAT CGACTAATTAG GTGTAAAAGAT TCGTCTTGTTA TTTTCTACCAA ATTATGAAATT TA | 1,000 | SEQ ID NO: 82 |
| | N916263 | TATAGGGCCAG ATAAACCATGA TAATCATAGGA TATTTGCAGAA ATCTTAAATTT CTGAGATTGCC AACAGAAGA | 1,000 | SEQ ID NO: 83 |
| | N917579 | TATGGATCTTC CAGTTGATTAC TGTTCTTTCGC TCCGCTTTTTG CTTTTTTACTC GTGA | 1,000 | SEQ ID NO: 84 |
| | N918080 | TACTCGTGAGG GTCCATCTATG ACCTATCCTGT GTTCTTTACTA GCGAAA | 1,000 | SEQ ID NO: 85 |

In addition, in tables 1 to 7, "Linkage group" represents the number given to each group among a plurality of linkage groups specified by QTL analysis. In tables 1 to 7, "Marker name" represents the name given to each marker originally obtained in the present invention. In tables 1 to 7, "Signal threshold" represents a threshold used for determination of the presence or absence of a marker.

In addition, the peak contained in the 18.7-cM region is present in a region sandwiched between a marker (N804607) consisting of the nucleotide sequence shown in SEQ ID NO: 5 and a marker (N815502) consisting of the nucleotide sequence shown in SEQ ID NO: 9. The peak contained in the 39.2-cM region is present in a region sandwiched between a marker (N803928) consisting of the nucleotide sequence shown in SEQ ID NO: 18 and a marker (N826906) consisting of the nucleotide sequence shown in SEQ ID NO: 22. The peak contained in the 19.2-cM region is present in a region sandwiched between a marker (N829378) consisting of the nucleotide sequence shown in SEQ ID NO: 25 and a marker (N821999) consisting of the nucleotide sequence shown in SEQ ID NO: 32. The peak contained in the 32.0-cM region is present in a region sandwiched between a marker (N915070) consisting of the nucleotide sequence shown in SEQ ID NO: 33 and a marker (N918161) consisting of the nucleotide sequence shown in SEQ ID NO: 42. The peak contained in the 39.5-cM region is present in a region sandwiched between a marker (N911103) consisting of the nucleotide sequence shown in SEQ ID NO: 57 and a marker (N918344) consisting of the nucleotide sequence shown in SEQ ID NO: 59. The peak contained in the 53.4-cM region is present in a region sandwiched between a marker (N918761) consisting of the nucleotide sequence shown in SEQ ID NO: 64 and a marker (N900663) consisting of the nucleotide sequence shown in SEQ ID NO: 66. The peak contained in the 38.0-cM region is present in a region sandwiched between a marker (N901524) consisting of the nucleotide sequence shown in SEQ ID NO: 73 and a marker (N915180) consisting of the nucleotide sequence shown in SEQ ID NO: 80.

A continuous nucleic acid region existing in any of 7 regions containing markers shown in tables 1 to 7 can be used as a marker associated with resistance to sugarcane smut. The term "nucleic acid region" used herein refers to a region having a nucleotide sequence having 95% or less, preferably 90% or less, more preferably 80% or less, and most preferably 70% or less identity to a different region present on a sugarcane chromosome. If the identity of a nucleic acid region serving as a marker associated with resistance to sugarcane smut to a different region falls within the above range, the nucleic acid region can be specifically detected according to a standard method. The identity value described herein can be calculated using default parameters and BLAST® or a similar algorithm.

In addition, the base length of a nucleic acid region serving as a marker associated with resistance to sugarcane smut can be at least 8 bases, preferably 15 bases or more, more preferably 20 bases or more, and most preferably 30 bases. If the base length of a nucleic acid region serving as a marker associated with resistance to sugarcane smut falls within the above range, the nucleic acid region can be specifically detected according to a standard method.

In particular, among the 14 types of markers contained in the 18.7-cM region, a marker associated with resistance to sugarcane smut is preferably designated as existing in the region sandwiched between the nucleotide sequence shown in SEQ ID NO: 5 and the nucleotide sequence shown in SEQ ID NO: 9. This is because the above peak is present in the region sandwiched between the nucleotide sequence shown in SEQ ID NO: 5 and the nucleotide sequence shown in SEQ ID NO: 9. In addition, among the 8 types of markers contained in the 39.2-cM region, a marker associated with resistance to sugarcane smut is preferably designated as existing in the region sandwiched between the nucleotide sequence shown in SEQ ID NO: 18 and the nucleotide sequence shown in SEQ ID NO: 22. This is because the above peak is present in the region sandwiched between the nucleotide sequence shown in SEQ ID NO: 18 and the nucleotide sequence shown in SEQ ID NO: 22. Further, among the 10 types of markers contained in the 19.2-cM region, a marker associated with resistance to sugarcane smut is preferably designated as existing in the region sandwiched between the nucleotide sequence shown in SEQ ID NO: 25 and the nucleotide sequence shown in SEQ ID NO: 32. This is because the above peak is present in the region sandwiched between the nucleotide sequence shown in SEQ ID NO: 25 and the nucleotide sequence shown in SEQ ID NO: 30. Furthermore, among the 19 types of markers contained in the 32.0-cM region, a marker associated with resistance to sugarcane smut is preferably designated as existing in the region sandwiched between the nucleotide sequence shown in SEQ ID NO: 33 and the nucleotide sequence shown in SEQ ID NO: 42. This is because the above peak is present in the region sandwiched between the nucleotide sequence shown in SEQ ID NO: 33 and the nucleotide sequence shown in SEQ ID NO: 42. Moreover, among the 11 types of markers contained in the 39.5-cM region, a marker associated with resistance to sugarcane smut is preferably designated as existing in the region sandwiched between the nucleotide sequence shown in SEQ ID NO: 57 and the nucleotide sequence shown in SEQ ID NO: 59. This is because the above peak is present in the region sandwiched between the nucleotide sequence shown in SEQ ID NO: 57 and the nucleotide sequence shown in SEQ ID NO: 59. Among the 10 types of markers contained in the 53.4-cM region, a marker associated with resistance to sugarcane smut is preferably designated as existing in the region sandwiched between the nucleotide sequence shown in SEQ ID NO: 64 and the nucleotide sequence shown in SEQ ID NO: 66. This is because the above peak is present in the region sandwiched between the nucleotide sequence shown in SEQ ID NO: 64 and the nucleotide sequence shown in SEQ ID NO: 66. Among the 13 types of markers contained in the 38.0-cM region, a marker associated with resistance to sugarcane smut is preferably designated as existing in the region sandwiched between the nucleotide sequence shown in SEQ ID NO: 73 and the nucleotide sequence shown in SEQ ID NO: 80. This is because the above peak is present in the region sandwiched between the nucleotide sequence shown in SEQ ID NO: 73 and the nucleotide sequence shown in SEQ ID NO: 80.

In addition, a nucleic acid region containing a single marker selected from among the 85 types of markers shown in tables 1 to 7 can be used as a marker associated with resistance to sugarcane smut. For example, it is preferable to use, as a marker associated with resistance to sugarcane smut, a nucleic acid region containing a marker (N802870) consisting of the nucleotide sequence shown in SEQ ID NO: 6 located closest to the peak position in the 18.7-cM region, a nucleic acid region containing a marker (N826906) consisting of the nucleotide sequence shown in SEQ ID NO: 22 located closest to the peak position in the 39.2-cM region, a nucleic acid region containing a marker (N821999) consisting of the nucleotide sequence shown in SEQ ID NO: 32 located closest to the peak position in the 19.2-cM region, a nucleic acid region containing a marker (N916186) consisting of the nucleotide sequence shown in SEQ ID NO: 35 located closest to the peak position in the 32.0-cM region, a nucleic acid region containing a marker (N918508) consisting of the nucleotide sequence shown in SEQ ID NO: 58 located closest to the peak position in the 39.5-cM region, a nucleic acid region containing a marker (N913735) consisting of the nucleotide sequence shown in SEQ ID NO: 65 located closest to the peak position in the 53.4-cM region, or a nucleic acid region containing a marker (N901163) consisting of the nucleotide sequence shown in SEQ ID NO: 74 located closest to the peak position in the 38.0-cM region. In such case, the nucleotide sequence of a nucleic acid region containing the marker can be specified by flanking sequence analysis such as inverse PCR analysis using primers designed based on the nucleotide sequence of such marker.

Further, as a marker associated with resistance to sugarcane smut, any of the above 85 types of markers can be directly used. Specifically, one or more type(s) of markers selected from among the 85 types of such markers can be directly used as a marker associated with resistance to sugarcane smut. For example, it is preferable to use, as a marker associated with resistance to sugarcane smut, a marker (N802870) consisting of the nucleotide sequence shown in SEQ ID NO: 6 located closest to the peak position in the 18.7-cM region, a marker (N826906) consisting of the nucleotide sequence shown in SEQ ID NO: 22 located closest to the peak position in the 39.2-cM region, a marker (N821999) consisting of the nucleotide sequence shown in SEQ ID NO: 32 located closest to the peak position in the 19.2-cM region, a marker (N916186) consisting of the nucleotide sequence shown in SEQ ID NO: 35 located closest to the peak position in the 32.0-cM region, a marker (N918508) consisting of the nucleotide sequence shown in SEQ ID NO: 58 located closest to the peak position in the 39.5-cM region, a marker (N913735) consisting of the nucleotide sequence shown in SEQ ID NO: 65 located closest to the peak position in the 53.4-cM region, or a marker (N901163) consisting of the nucleotide sequence shown in SEQ ID NO: 74 located closest to the peak position in the 38.0-cM region.

<Sugarcane Marker Identification>

As described above, markers associated with resistance to sugarcane smut were identified from among 3004 markers and 4569 markers originally obtained from sugarcane chromosomes in the present invention. The 3004 markers and the 4569 markers are described below. Upon identification of these markers, a DNA microarray can be used according to the method disclosed in JP Patent Application No. 2009-283430.

Specifically, the 3004 markers and the 4569 markers originally obtained from sugarcane chromosomes are used with a DNA microarray having probes designed by the method disclosed in JP Patent Application No. 2009-283430. The method for designing probes as shown in FIG. 1 is described below. First, genomic DNA is extracted from sugarcane (step 1a). Next, the extracted genomic DNA is digested with a single or a plurality of restriction enzyme(s) (step 1b). In addition, in the example shown in FIG. 1, 2 types of restriction enzymes illustrated as restriction enzymes A and B are used (in the order of A first and then B) to digest genomic DNA. The restriction enzymes used herein are not particularly limited. However, examples of restriction enzymes that can be used include PstI, EcoRI, HindIII, BstNI, HpaII, and HaeIII. In particular, restriction enzymes can be adequately selected in consideration of the frequency of appearance of recognition sequences such that a genomic DNA fragment having a base length of 20 to 10000 can be obtained when genomic DNA is completely digested. In addition, when a plurality of restriction enzymes are used, it is preferable for a genomic DNA fragment obtained after the use of all restriction enzymes to have a base length of 200 to 6000. Further, when a plurality of restriction enzymes are used, the order in which restriction enzymes are subjected to treatment is not particularly limited. In addition, a plurality of restriction enzymes may be used in an identical reaction system if they are treated under identical conditions (e.g., solution composition and temperature). Specifically, in the example shown in FIG. 1, genomic DNA is digested using restriction enzymes A and B in such order. However, genomic DNA may be digested by simultaneously using restriction enzymes A and B in an identical reaction system. Alternatively, genomic DNA may be digested using restriction enzymes B and A in such order. Further, 3 or more restriction enzymes may be used.

Next, adapters are bound to a genomic DNA fragment subjected to restriction enzyme treatment (step 1c). The adapter used herein is not particularly limited as long as it can be bound to both ends of a genomic DNA fragment obtained by the above restriction enzyme treatment. For example, it is possible to use, as an adapter, an adapter having a single strand complementary to a protruding end (sticky end) formed at each end of genomic DNA by restriction enzyme treatment and a primer binding sequence to which a primer used upon amplification treatment as described in detail below can hybridize. In addition, it is also possible to use, as an adapter, an adapter having a single strand complementary to the above protruding end (sticky end) and a restriction enzyme recognition site that is incorporated into a vector upon cloning.

In addition, when genomic DNA is digested using a plurality of restriction enzymes, a plurality of adapters corresponding to the relevant restriction enzymes can be prepared and used. Specifically, it is possible to use a plurality of adapters having single strands complementary to different protruding ends formed upon digestion of genomic DNA with a plurality of restriction enzymes. Here, a plurality of adapters corresponding to a plurality of restriction enzymes each may have a common primer binding sequence such that a common primer can hybridize to each such adapter. Alternatively, they may have different primer binding sequences such that different primers can separately hybridize thereto.

Further, when genomic DNA is digested using a plurality of restriction enzymes, it is possible to prepare and use, as an adaptor, adapter(s) corresponding to one or a part of restriction enzyme(s) selected from among a plurality of the used restriction enzymes.

Next, a genomic DNA fragment to both ends of which adapters have been added is amplified (step 1d). When an adapter having a primer binding sequence is used, the genomic DNA fragment can be amplified using a primer that can hybridize to the primer binding sequence. Alternatively, a genomic DNA fragment to which an adapter has been added is cloned into a vector using the adapter sequence. The genomic DNA fragment can be amplified using primers that can hybridize to specific regions of the vector. In addition, as an example, PCR can be used for a genomic DNA fragment amplification reaction using primers.

When genomic DNA is digested using a plurality of restriction enzymes and a plurality of adapters corresponding to the relevant restriction enzymes are ligated to genomic DNA fragments, the adapters are ligated to all genomic DNA fragments obtained by treatment with a plurality of restriction enzymes. In this case, all the obtained genomic DNA fragments can be amplified by carrying out a nucleic acid amplification reaction using primer binding sequences contained in adapters.

Alternatively, when genomic DNA is digested using a plurality of restriction enzymes, followed by ligation of adapter(s) corresponding to one or a part of restriction enzyme(s) selected from among a plurality of the used restriction enzymes to genomic DNA fragments, among the obtained genomic DNA fragments, a genomic DNA fragment to both ends of which the selected restriction enzyme recognition sequences have been ligated can be exclusively amplified.

Next, the nucleotide sequence of the amplified genomic DNA fragment is determined (step 1e). Then, one or more region, which has a base length shorter than the base length of the genomic DNA fragment and corresponds to at least a partial region of the genomic DNA fragment, is specified. Sugarcane probes are designed using at least one of the thus specified regions (step 1f). A method for determining the nucleotide sequence of a genomic DNA fragment is not particularly limited. A conventionally known method using a DNA sequencer applied to the Sanger method or the like can be used. For example, a region to be designed herein has a 20- to 100-base length, preferably a 30- to 90-base length, and more preferably a 50- to 75-base length as described above.

A DNA microarray can be produced by designing many probes using genomic DNA extracted from sugarcane as described above and synthesizing an oligonucleotide having a desired nucleotide sequence on a support based on the nucleotide sequence of the designed probe. With the use of a DNA microarray prepared as described above, the 3004 markers and the 4569 markers, including the above 85 types of markers associated with resistance to sugarcane smut shown in SEQ ID NOS: 1 to 85, can be identified.

More specifically, the present inventors obtained signal data of known sugarcane varieties (NiF8 and Ni9) and a progeny line (line 191) obtained by crossing the varieties with the use of the DNA microarray described above. Then, genotype data were obtained based on the obtained signal data. Based on the obtained genotype data, chromosomal marker position information was obtained by calculation using the gene distance function (Kosambi) and the AntMap genetic map creation software (Iwata H, Ninomiya S (2006) AntMap: constructing genetic linkage maps using an ant colony optimization algorithm, Breed Sci 56: 371-378). Further, a genetic map datasheet was created based on the obtained marker position information using Mapmaker/EXP ver. 3.0 (A Whitehead Institute for Biomedical Research Technical Report, Third Edition, January, 1993). As a result, the 3004 markers and the 4569 markers, including the aforementioned 85 types of markers associated with resistance to sugarcane smut shown in SEQ ID NOS: 1 to 85, were identified.

<Use of Markers Associated with Resistance to Sugarcane Smut>

The use of markers associated with resistance to sugarcane smut makes it possible to determine whether a sugarcane progeny line or the like, which has a phenotype exhibiting unknown smut resistance, is a line having a phenotype showing the improvement of smut resistance. The expression "the use of markers associated with resistance to sugarcane smut" used herein indicates the use of a DNA microarray having probes corresponding to markers associated with resistance to sugarcane smut in one embodiment. The expression "probes corresponding to markers associated with resistance to sugarcane smut" indicates oligonucleotides that can specifically hybridize under stringent conditions to markers associated with resistance to sugarcane smut defined as above. For instance, such oligonucleotides can be designed as partial or whole regions with base lengths of at least 10 continuous bases, continuous bases, 20 continuous bases, 25 continuous bases, 30 continuous bases, 35 continuous bases, 40 continuous bases, 45 continuous bases, or 50 or more continuous bases of the nucleotide sequences or complementary strands thereof of markers associated with resistance to sugarcane smut defined as above. In addition, a DNA microarray having such probes may be any type of microarray, such as a microarray having a planar substrate comprising glass, silicone, or the like as a carrier, a bead array comprising microbeads as carriers, or a three-dimensional microarray having an inner wall comprising hollow fibers to which probes are fixed.

The use of a DNA microarray prepared as described above makes it possible to determine whether a sugarcane line such as a progeny line or the like, which has a phenotype exhibiting unknown smut resistance, is a line having a phenotype showing the improvement of smut resistance. In addition, in the case of a method other than the above method involving the use of a DNA microarray, it is also possible to determine whether a sugarcane line, which has a phenotype exhibiting unknown smut resistance, is a line having a trait characterized by the improvement of smut resistance by detecting the above markers associated with resistance to sugarcane smut by a conventionally known method.

Figure 2:
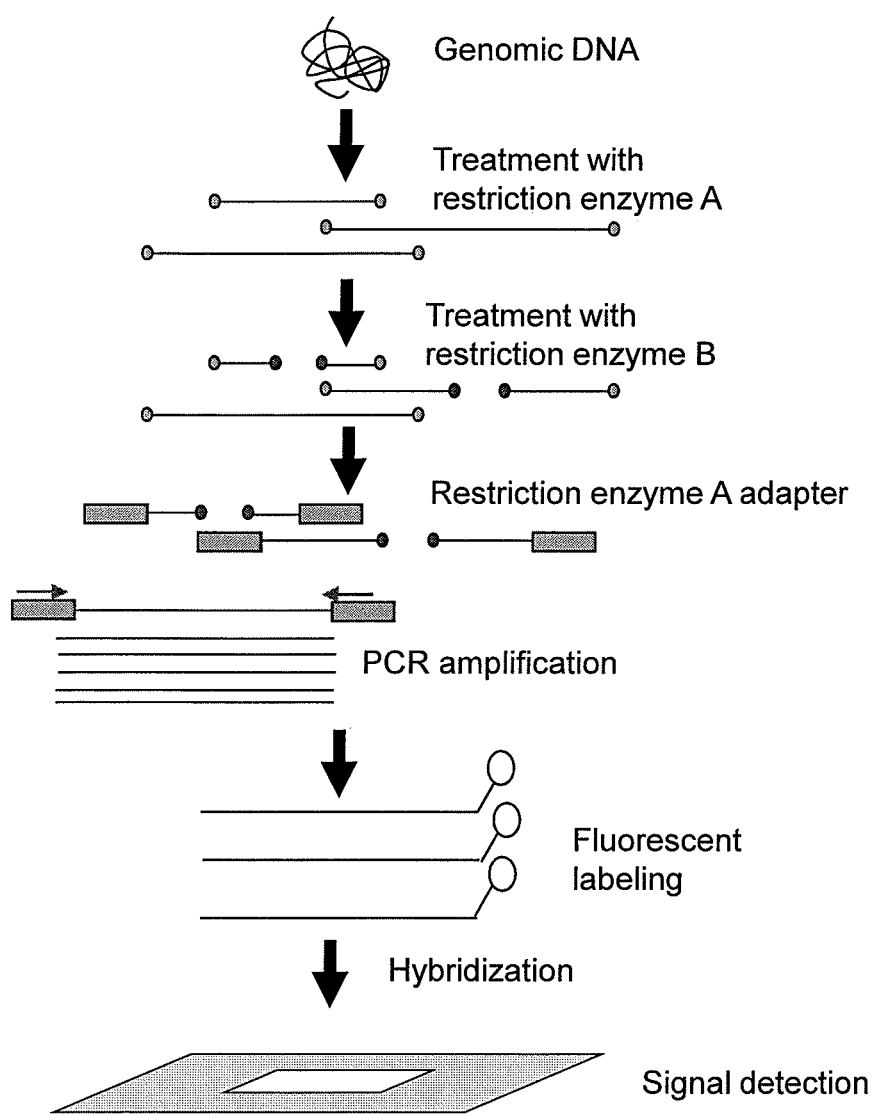
FIG. 2 schematically shows a step of signal detection with the use of a DNA microarray.
Figure 3:
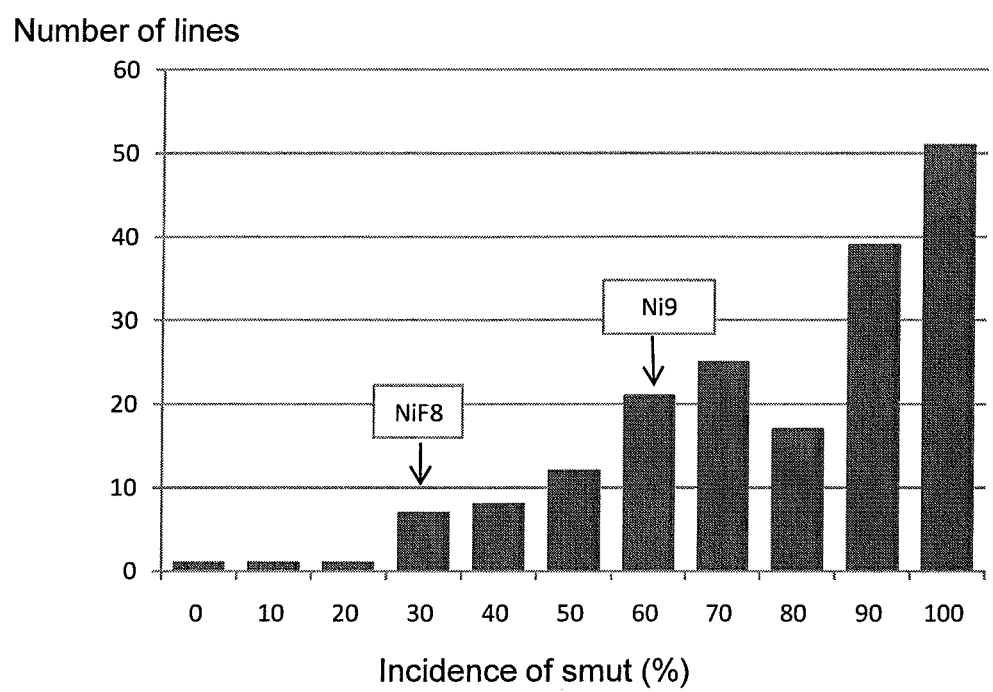
FIG. 3 is a characteristic chart showing data on smut resistance examined on Jun. 23, 2010, for sugarcane variety/line groups used in the Examples.
Figure 4:
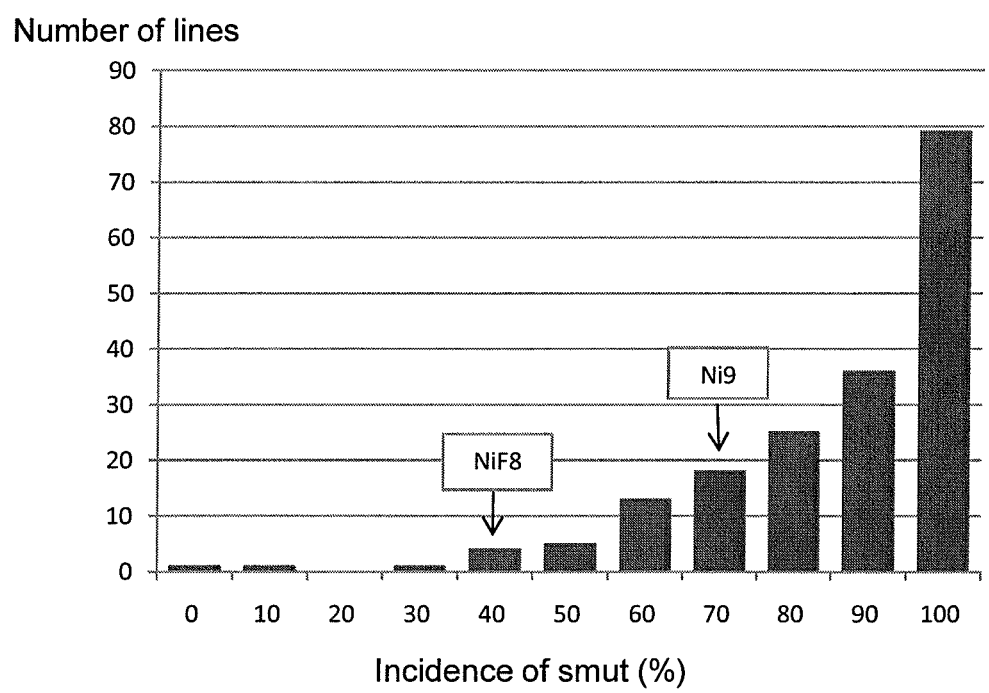
FIG. 4 is a characteristic chart showing data on smut resistance examined on Jul. 21, 2010, for sugarcane variety/line groups used in the Examples.
Figure 5:
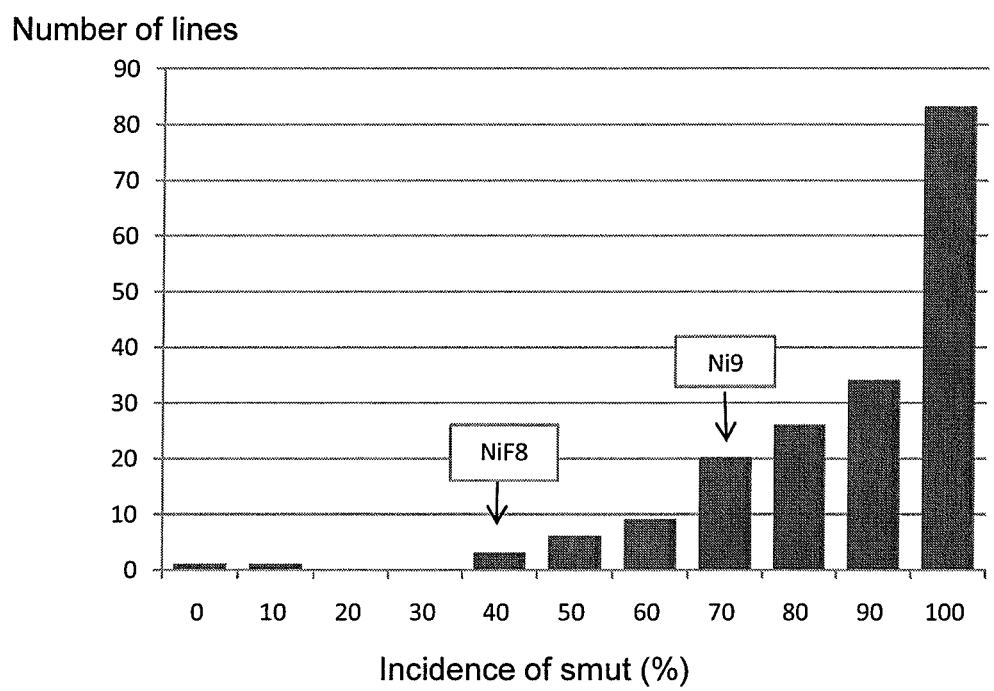
FIG. 5 is a characteristic chart showing data on smut resistance examined on Aug. 18, 2010, for sugarcane variety/line groups used in the Examples.
Figure 6:
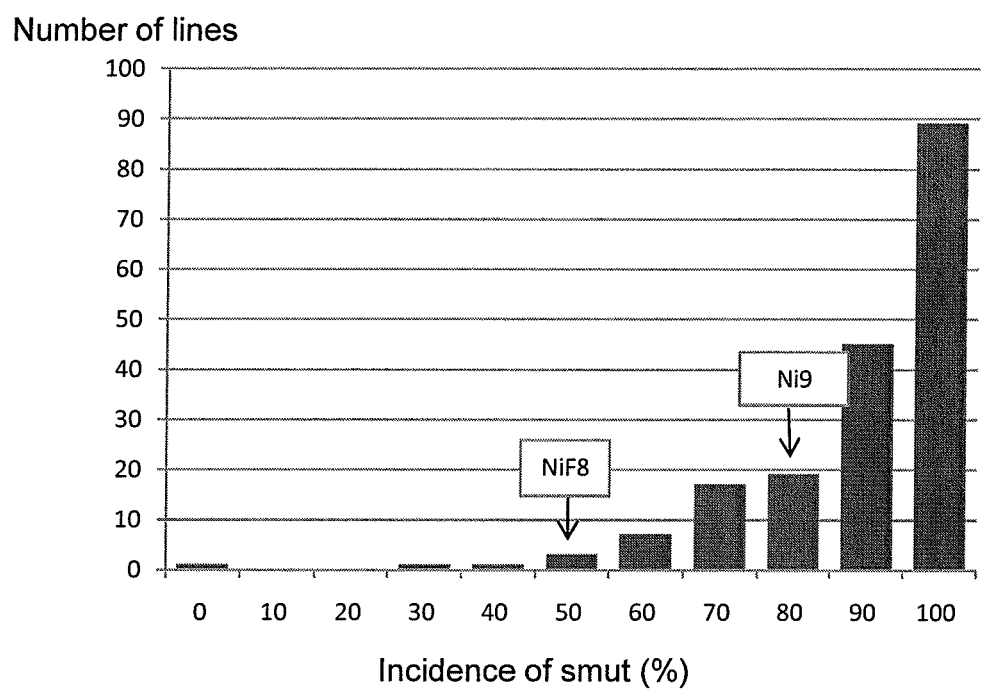
FIG. 6 is a characteristic chart showing data on smut resistance examined on Sep. 2, 2010, for sugarcane variety/line groups used in the Examples.
Figure 7:
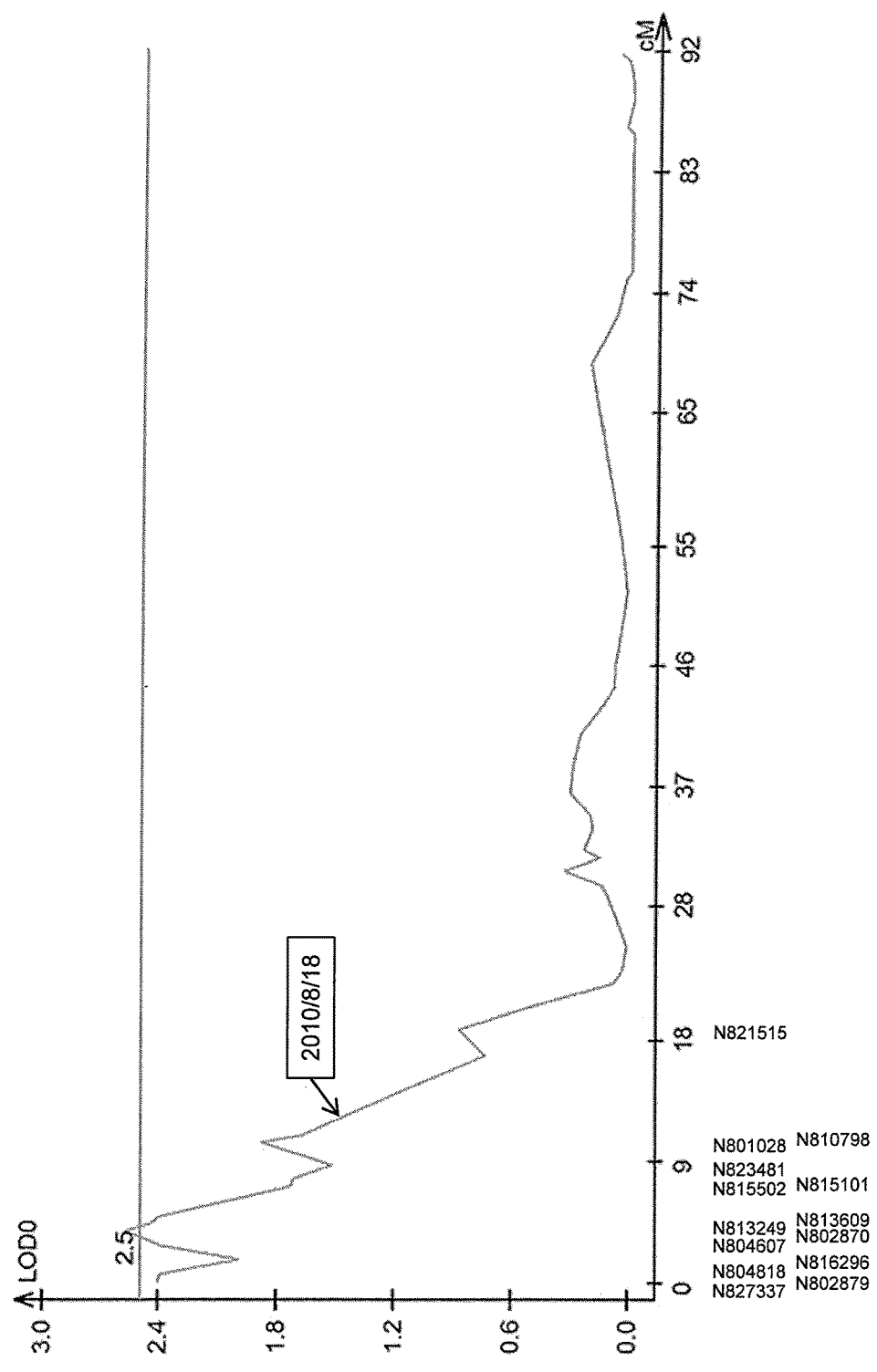
FIG. 7 is a characteristic chart showing QTL analysis results regarding smut resistance (the 5th linkage group in NiF8).
Figure 8:
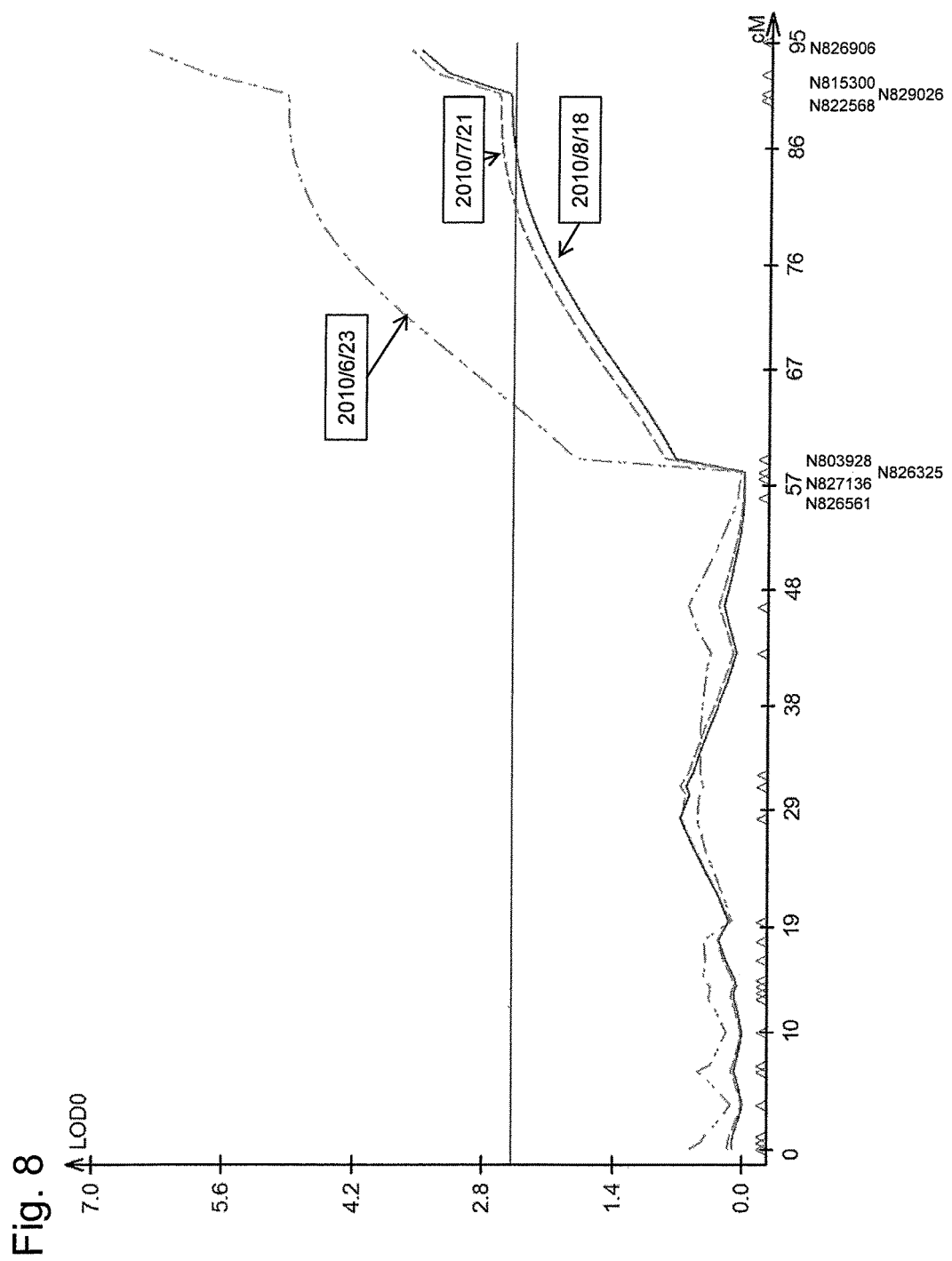
FIG. 8 is a characteristic chart showing QTL analysis results regarding smut resistance (the 17th linkage group in NiF8).
Figure 9:
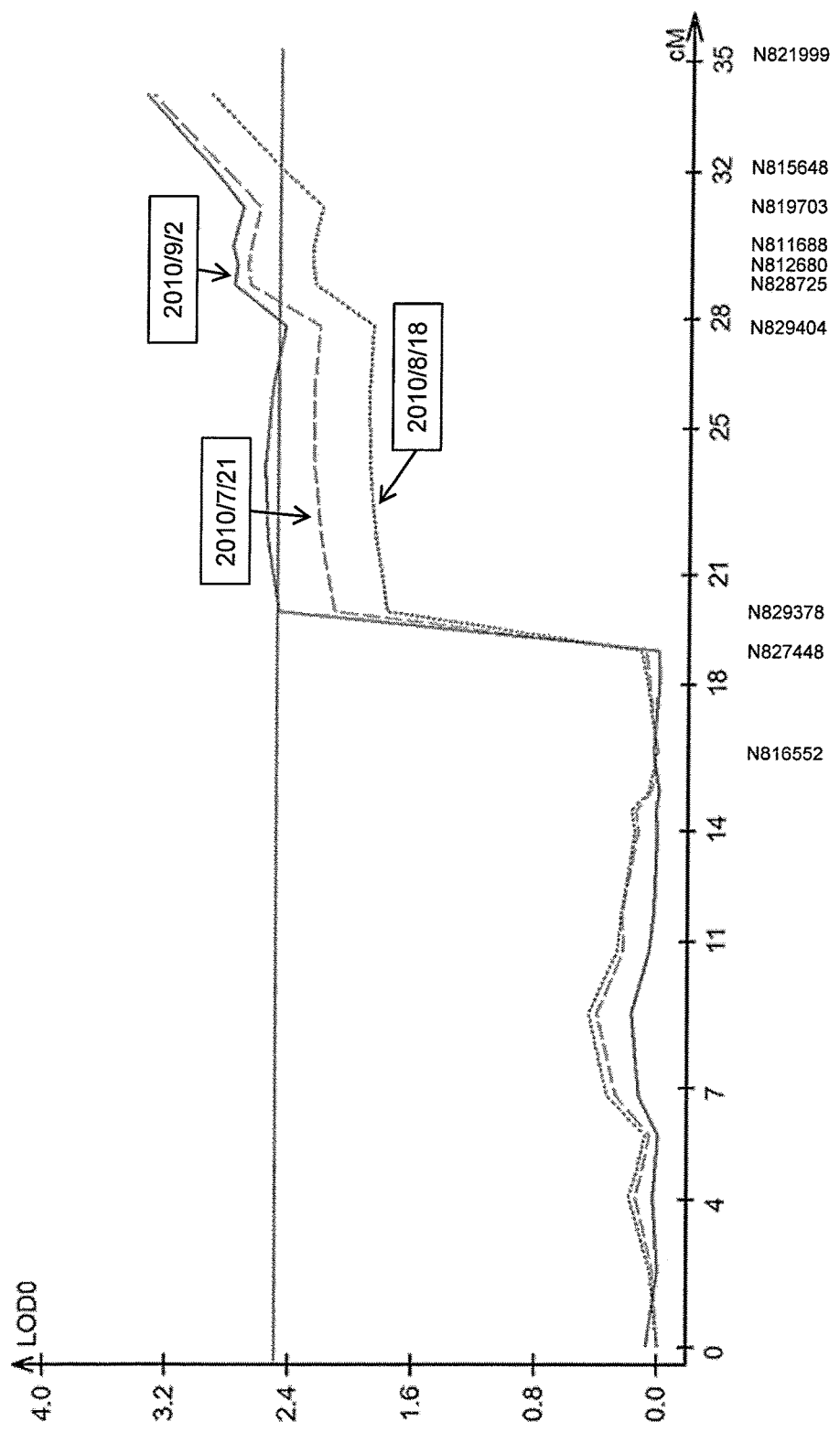
FIG. 9 is a characteristic chart showing QTL analysis results regarding smut resistance (the 40th linkage group in NiF8).
Figure 10:
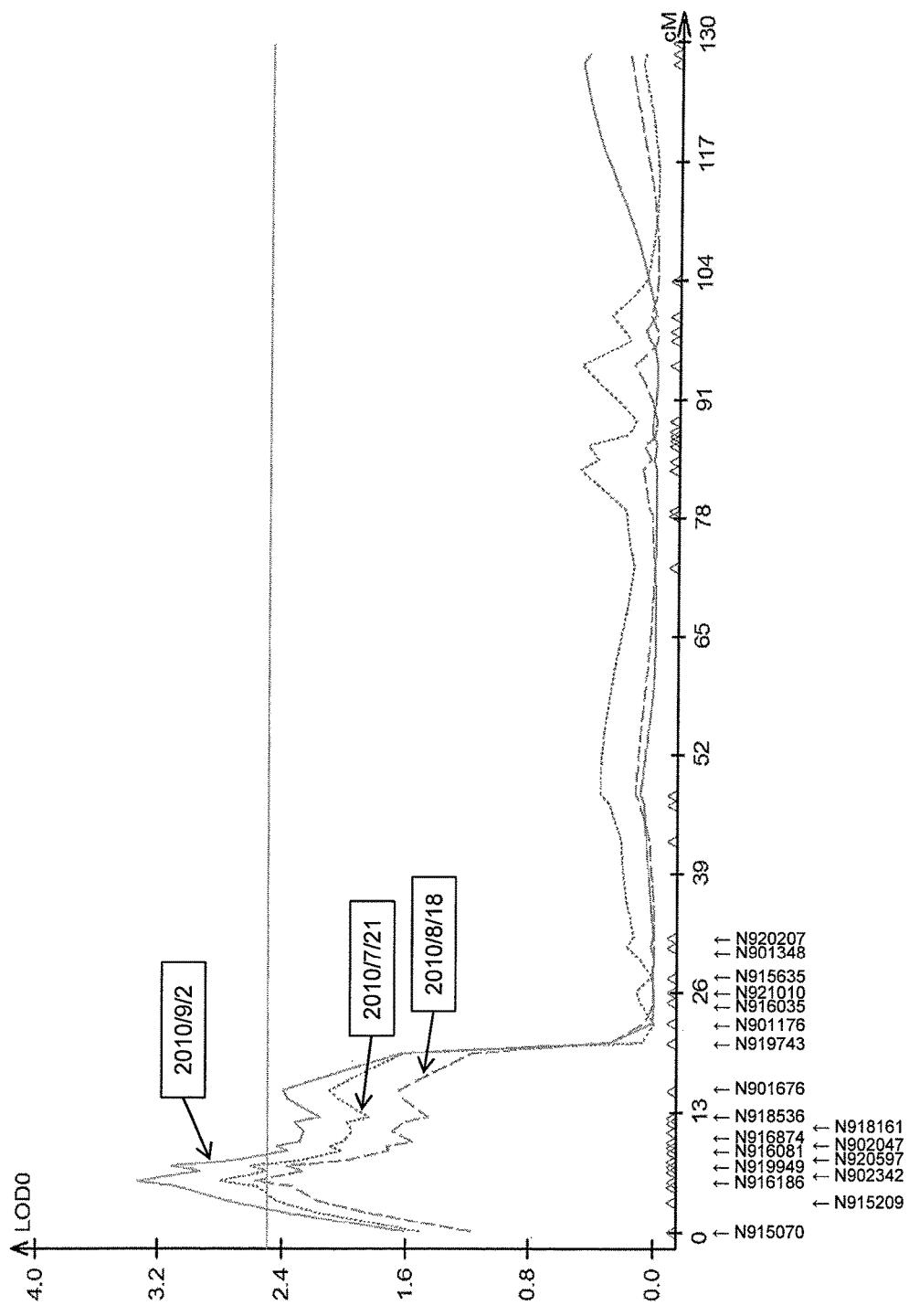
FIG. 10 is a characteristic chart showing QTL analysis results regarding smut resistance (the 1st linkage group in Ni9).
Figure 11:
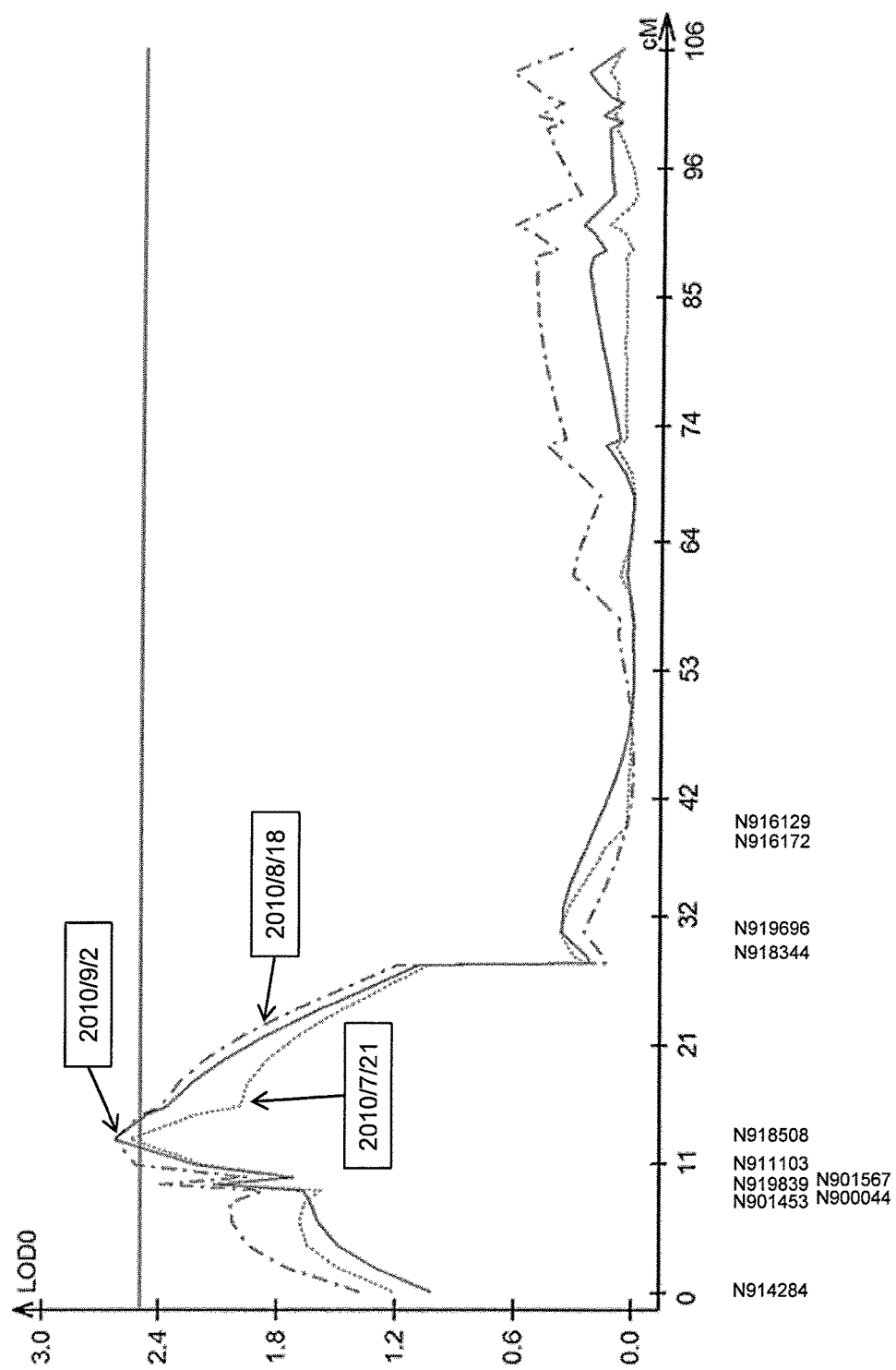
FIG. 11 is a characteristic chart showing QTL analysis results regarding smut resistance (the 13th linkage group in Ni9).
Figure 12:
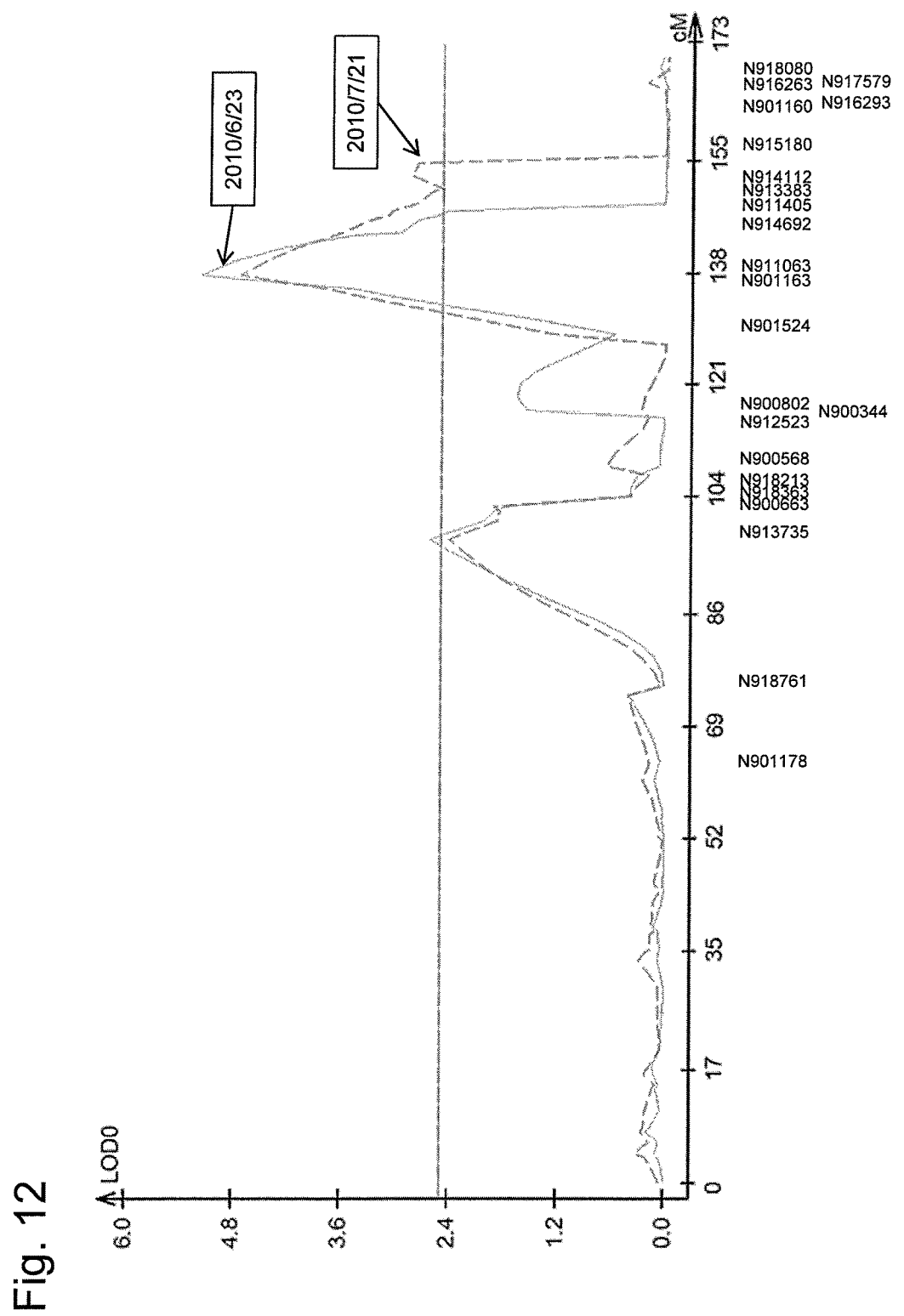
FIG. 12 is a characteristic chart showing QTL analysis results regarding smut resistance (the 14th linkage group in Ni9).

The method involving the use of a DNA microarray is described in more detail. As shown in FIG. 2, first, genomic DNA is extracted from a sugarcane sample. In this case, a sugarcane sample is a sugarcane line such as a sugarcane progeny line, which has a phenotype exhibiting unknown smut resistance, and/or a sugarcane line used as a parent for producing a progeny line, and thus which can be used as a subject to be determined whether to have a trait characterized by the improvement of smut resistance or not. In addition, it is also possible to evaluate smut resistance in a sample plant which is a non-sugarcane plant such as a graminaceous plant (e.g., *Sorghum* or *Erianthus*).

Next, a plurality of genomic DNA fragments are prepared by digesting the extracted genomic DNA with restriction enzymes used for preparing the DNA microarray. Then, the obtained genomic DNA fragments are ligated to adapters used for preparation of the DNA microarray. Subsequently, the genomic DNA fragments, to both ends of which adapters have been added, are amplified using primers employed for preparation of the DNA microarray. Accordingly, sugarcane-sample-derived genomic DNA fragments corresponding to the genomic DNA fragments amplified in step 1d upon preparation of the DNA microarray can be amplified.

In this step, among the genomic DNA fragments to which adapters have been added, specific genomic DNA fragments may be selectively amplified. For instance, in a case in which a plurality of adapters corresponding to a plurality of restriction enzymes are used, genomic DNA fragments to which specific adapters have been added can be selectively amplified. In addition, when genomic DNA is digested with a plurality of restriction enzymes, genomic DNA fragments to which adapters have been added can be selectively amplified by adding adapters only to genomic DNA fragments that have protruding ends corresponding to specific restriction enzymes among the obtained genomic DNA fragments. Thus, specific DNA fragment concentration can be increased by selectively amplifying the specific genomic DNA fragments.

Thereafter, amplified genomic DNA fragments are labeled. Any conventionally known substance may be used as a labeling substance. Examples of a labeling substance that can be used include fluorescent molecules, dye molecules, and radioactive molecules. In addition, this step can be omitted using a labeled nucleotide in the step of amplifying genomic DNA fragments. This is because when genomic DNA fragments are amplified using a labeled nucleotide in the amplification step, amplified DNA fragments can be labeled.

Next, labeled genomic DNA fragments are allowed to come into contact with the DNA microarray under certain conditions such that probes fixed to the DNA microarray hybridize to the labeled genomic DNA fragments. At such time, preferably, highly stringent conditions are provided for hybridization. Under highly stringent conditions, it becomes possible to determine with high accuracy whether or not markers associated with resistance to sugarcane smut are present in a sugarcane sample. In addition, stringent conditions can be adjusted based on reaction temperature and salt concentration. That is, an increase in temperature or a decrease in salt concentration results in more stringent conditions. For example, when a probe having a length of 50 to 75 bases is used, the following more stringent conditions can be provided as hybridization conditions: 40 degrees C. to 44 degrees C.; 0.21 SDS; and 6×SSC.

In addition, hybridization between labeled genomic DNA fragments and probes can be confirmed by detecting a labeling substance. Specifically, after the above hybridization reaction of labeled genomic DNA fragments and probes, unreacted genomic DNA fragments and the like are washed, and the labeling substance bound to each genomic DNA fragment specifically hybridizing to a probe is observed. For instance, in a case in which the labeling substance is a fluorescent material, the fluorescence wavelength is detected. In a case in which the labeling substance is a dye molecule, the dye wavelength is detected. More specifically, apparatuses such as fluorescent detectors and image analyzers used for conventional DNA microarray analysis can be used.

As described above, it is possible to determine whether or not a sugarcane sample has the above markers associated with resistance to sugarcane smut with the use of the DNA microarray. Here, as described above, as the marker associated with resistance to sugarcane smut, a marker linked to a trait characterized by the improvement of smut resistance and a marker linked to a trait characterized by the reduction of smut resistance are provided. Markers associated with resistance to sugarcane smut designed based on the three aforementioned regions identified in tables 2, 4, and 7 are linked to a trait characterized by the improvement of smut resistance. Meanwhile, markers associated with resistance to sugarcane smut designed based on the four aforementioned regions identified in tables 1, 3, 5, and 6 are linked to a trait characterized by the reduction of smut resistance.

Therefore, if any one of the markers associated with resistance to sugarcane smut designed based on the three aforementioned regions identified in tables 2, 4, and 7 is present in a sugarcane sample, it is possible to determine that the sample is of a variety with improved smut resistance. Further, if any one of the markers associated with resistance to sugarcane smut designed based on the four aforementioned regions identified in tables 1, 3, 5, and 6 is absent in a sugarcane sample, it is possible to determine that the sample is of a variety with improved smut resistance. Preferably, if any one of the markers associated with resistance to sugarcane smut designed based on the three aforementioned regions identified in tables 2, 4, and 7 is present in a sugarcane sample, and if any one of the markers associated with resistance to sugarcane smut designed based on the four aforementioned regions identified in tables 1, 3, 5, and 6 is absent in the sugarcane sample, it is possible to determine with high accuracy that the sample is of a variety with improved smut resistance.

In particular, according to the method described above, it is not necessary to cultivate sugarcane samples to such an extent that determination using an actual smut resistance test becomes possible. For instance, seeds of a progeny line or a young seedling obtained as a result of germination of such seeds can be used. Therefore, the area of a field used for cultivation of sugarcane samples and other factors such as cost of cultivation can be significantly reduced with the use of the markers associated with resistance to sugarcane smut. In addition, the use of markers associated with resistance to sugarcane smut makes it possible to reduce the cost of facilities such as a large-scale special-purpose greenhouse, a special-purpose field, or isolation facility from an external environment, without the need to actually cause infection with a causative microorganism of smut (*Ustilago scitaminea*).

In particular, when a novel sugarcane variety is created, it is preferable to produce several tens of thousands of seedlings via crossing and then to identify a novel sugarcane variety using markers associated with resistance to sugarcane smut prior to or instead of seedling selection. The use of such markers associated with resistance to sugarcane smut makes it possible to significantly reduce the number of excellent lines that need to be cultivated in an actual field. This allows drastic reduction of time-consuming efforts and the cost required to create a novel sugarcane variety.

Alternatively, upon creation of a new sugarcane variety, firstly, it may be determined whether or not a marker associated with resistance to sugarcane smut is present in a parent variety used for crossing, thereby allowing selection of a parent variety with excellent smut resistance. It can be expected that a progeny line with excellent smut resistance will be obtained with high frequency by creating a parent variety with excellent smut resistance on a priority basis. The use of such marker(s) associated with resistance to sugarcane smut makes it possible to significantly reduce the number of excellent lines that need to be cultivated. This allows drastic reduction of time-consuming efforts and the cost required to create a novel sugarcane variety.

EXAMPLES

The present invention is hereafter described in greater detail with reference to the following examples, although the technical scope of the present invention is not limited thereto.

1. Production of DNA Microarray Probes (1) Materials

The following varieties were used: sugarcane varieties: NiF8, Ni9, US56-15-8, POJ2878, Q165, R570, Co290 and B3439; closely-related sugarcane wild-type varieties: Glagah Kloet, Chunee, Natal Uba, and Robustum 9; and *Erianthus* varieties: IJ76-349 and JW630.

(2) Restriction Enzyme Treatment

Genomic DNA was extracted from each of the above sugarcane varieties, closely-related sugarcane wild-type varieties, and *Erianthus* varieties using DNeasy Plant Mini Kits (Qiagen). Genomic DNAs (750 ng each) were treated with a PstI restriction enzyme (NEB; 25 units) at 37 degrees C. for 2 hours. A BstNI restriction enzyme (NEB; 25 units) was added thereto, followed by treatment at 60 degrees C. for 2 hours.

(3) Adapter Ligation

PstI sequence adapters (5'-CACGATGGATCCAGTGCA-3' (SEQ ID NO: 86) and 5'-CTGGATCCATCGTGCA-3' (SEQ ID NO: 87)) and T4 DNA Ligase (NEB; 800 units) were added to the genomic DNA fragments treated in (2) (120 ng each), and the obtained mixtures were subjected to treatment at 16 degrees C. overnight. Thus, the adapters were selectively added to genomic DNA fragments having PstI recognition sequences at both ends thereof among the genomic DNA fragments treated in (2).

(4) PCR Amplification

A PstI sequence adapter recognition primer (5'-GATGGATCCAGTGCAG-3' (SEQ ID NO: 88)) and Taq polymerase (TAKARA; PrimeSTAR; 1.25 units) were added to the genomic DNA fragment (15 ng) having the adaptors obtained in (3). Then, the genomic DNA fragment was amplified by PCR (treatment at 98 degrees C. for 10 seconds, 55 degrees C. for 15 seconds, 72 degrees C. for 1 minute for 30 cycles, and then at 72 degrees C. for 3 minutes, followed by storage at 4 degrees C.).

(5) Genome Sequence Acquisition

The nucleotide sequence of the genomic DNA fragment subjected to PCR amplification in (4) was determined by the Sanger method. In addition, information on a nucleotide sequence sandwiched between PstI recognition sequences was obtained based on the total *sorghum* genome sequence information contained in the genome database (Gramene).

(6) Probe Design and DNA Microarray Production 50- to 75-bp probes were designed based on the genome sequence information in (5). Based on the nucleotide sequence information of the designed probes, a DNA microarray having the probes was produced.

2. Acquisition of Signal Data Using a DNA Microarray
(1) Materials

Sugarcane varieties/lines (NiF8 and Ni9) and the progeny line (line 191) were used.

(2) Restriction Enzyme Treatment

Genomic DNAs were extracted from NiF8, Ni9, and the progeny line (line 191) using DNeasy Plant Mini Kits (Qiagen). Genomic DNAs (750 ng each) were treated with a PstI restriction enzyme (NEB; 25 units) at 37 degrees C. for 2 hours. Then, a BstNI restriction enzyme (NEB; 25 units) was added thereto, followed by treatment at 60 degrees C. for 2 hours.

(3) Adapter Ligation

PstI sequence adapters (5'-CACGATGGATCCAGTGCA-3' (SEQ ID NO: 86) and 5'-CTGGATCCATCGTGCA-3' (SEQ ID NO: 87)) and T4 DNA Ligase (NEB; 800 units) were added to the genomic DNA fragments treated in (2) (120 ng each), and the obtained mixtures were treated at 16 degrees C. overnight. Thus, the adaptors were selectively added to a genomic DNA fragment having PstI recognition sequences at both ends thereof among the genomic DNA fragments treated in (2).

(4) PCR Amplification

A PstI sequence adapter recognition primer (5'-GATG-GATCCAGTGCAG-3' (SEQ ID NO: 88)) and Taq polymerase (TAKARA; PrimeSTAR; 1.25 units) were added to the genomic DNA fragment (15 ng) having the adapters obtained in (3). Then, the genomic DNA fragment was amplified by PCR (treatment at 98 degrees C. for 10 seconds, 55 degrees C. for 15 seconds, 72 degrees C. for 1 minute for 30 cycles, and then 72 degrees C. for 3 minutes, followed by storage at 4 degrees C.).

(5) Labeling

The PCR amplification fragment obtained in (4) above was purified with a column (Qiagen). Cy3-labeled 9mers (TriLink; 1 O.D.) was added thereto. The resultant was treated at 98 degrees C. for 10 minutes and allowed to stand still on ice for 10 minutes. Then, Klenow (NEB; 100 units) was added thereto, followed by treatment at 37 degrees C. for 2 hours. Thereafter, a labeled sample was prepared by ethanol precipitation.

(6) Hybridization/Signal Detection

The labeled sample obtained in (5) was subjected to hybridization using the DNA microarray prepared in 1 above in accordance with the NimbleGen Array User's Guide. Signals from the label were detected.

3. Identification of QTL for Sugarcane Smut Resistance and Development of Markers (1) Creation of Genetic Map Datasheet Genotype data of possible 3004 markers and 4569 markers were obtained based on the signal data detected in 2 above of the NiF8 and Ni9 sugarcane varieties and the progeny line (line 191). Based on the obtained genotype data, chromosomal marker position information was obtained by calculation using the gene distance function (Kosambi) and the AntMap genetic map creation software (Iwata H, Ninomiya S (2006) AntMap: constructing genetic linkage maps using an ant colony optimization algorithm, Breed Sci 56: 371-378). Further, a genetic map datasheet was created based on the obtained marker position information using Mapmaker/EXP ver. 3.0 (A Whitehead Institute for Biomedical Research Technical Report, Third Edition, January, 1993).

(2) Acquisition of Smut Resistance Data

From Oct. 26 to 28, 2009, stalks of NiF8, Ni9, and the 191 hybrid progeny line were harvested. They were subjected to treatment for stimulating germination at room temperature and high humidity for 2 to 3 days, followed by wound inoculation with smut spores. For wound inoculation, wounds were made on both sides of buds (6 wounds in total; approximately 4.0 mm in depth), and then a spore suspension ($10^7$ to $10^8$ spores/ml) was applied to the wounds using a brush. Smut spores in the spore suspension were collected from smut whips of Ni9 stocks naturally infected with smut, which were cultivated in Okinawa in 2009. Seedlings subjected to wound inoculation were cultivated for 2 to 3 days at room temperature and high humidity and planted in nursery boxes from October 30 to Nov. 1, 2009 (40 buds/box, 2 boxes/line). The planted seedlings were cultivated at high humidity in a greenhouse until Sep. 2, 2010. The degree of the development of smut was investigated by counting, as the number of affected seedlings, the number of seedlings showing a symptom of smut, which is the outgrowth of a smut whip from the apex of a stalk. After the count of the affected seedlings, the plant bodies of affected seedlings were harvested at the ground level so that they could be removed. The number of seedlings affected with smut was investigated on Jun. 23, Jul. 21, Aug. 18, and Sep. 2, 2010 for a total of four instances. The incidence of smut was calculated as a percentage of the number of germinating stocks (excluding stocks killed by non-smut causes) accounted for by the number of affected stocks. FIGS. 3, 4, 5, and 6 show the study results of Jun. 23, 2010, the study results of Jul. 21, 2010, the study results of Aug. 18, 2010, and the study results of Sep. 2, 2010, respectively.

(3) Quantitative Trait (Quantitative Trait Loci: QTL) Analysis

Based on the genetic map datasheet obtained in (1) above and the smut resistance data obtained in (2) above, QTL analysis was carried out by the composite interval mapping (CIM) method using the QTL Cartographer gene analysis software (Wang S., C. J. Basten, and Z.-B. Zeng (2010). Windows QTL Cartographer 2.5. Department of Statistics, North Carolina State University, Raleigh, N.C.). Upon analysis, the LOD threshold was determined to be 2.5. As a result, as shown in FIGS. 7 to 12, the presence of QTL regarding sugarcane smut resistance was confirmed in the following seven ranges: the range between markers N827337 and N821515 present in the 5th linkage group (August 18), the range between markers N826561 and N826906 present in the 17th linkage group (June 23, July 21, and August 18), and the range between markers N816552 and N821999 present in the 40th linkage group (July 21, August 18, and September 2) of the NiF8 sugarcane variety; the range between markers N915070 and N920207 present in the 1st linkage group (July 21, August 18, and September 2), the range between markers N914284 and N916129 present in the 13th linkage group (July 21, August 18, and September 2), and the range between markers N901177 and N900802 (June 23) and the range between markers N901524 and N918080 (June 23 and July 21) present in the 14th linkage group of the Ni9 sugarcane variety. Specifically, peaks exceeding the LOD threshold were observed in the above seven ranges. It was possible to specify the obtained peaks as shown in table 8, suggesting the presence of a causative gene (or a group of causative genes) having the function of causing the improvement of smut resistance at the each peak positions. In addition, the "Effect (%)" column in table 8 indicates an increase or a decrease in the incidence of smut. Therefore, if the value of "Effect (%)" is negative, it means that the QTL (quantitative trait locus) is linked to a trait characterized by the improvement of smut resistance. If the value of "Effect (%)" is positive, it means that the QTL is linked to a trait characterized by the reduction of smut resistance.

TABLE 8

| Variety | Linkage group | Investigation date | Position (cM) | Range (cM) | Close marker | LOD score | Effect (%) |
|---|---|---|---|---|---|---|---|
| NiF8 | 5 | 8/18 | 3.8 | 18.7 | N827337-N821515 | 2.6 | 8.2 |
| NiF8 | 17 | 6/23 | 94.3 | 39.2 | N826561-N826906 | 6.5 | −16.5 |
| NiF8 | 17 | 7/21 | 94.3 | 39.2 | N826561-N826906 | 3.6 | −10.1 |
| NiF8 | 17 | 8/18 | 94.3 | 39.2 | N826561-N826906 | 3.5 | −9.7 |
| NiF8 | 40 | 7/21 | 34.1 | 19.2 | N816552-N821999 | 3.3 | 9.6 |
| NiF8 | 40 | 8/18 | 34.1 | 19.2 | N816552-N821999 | 3.0 | 8.9 |
| NiF8 | 40 | 9/2 | 34.1 | 19.2 | N816552-N821999 | 3.4 | 8.4 |
| Ni9 | 1 | 7/21 | 5.5 | 32.0 | N915070-N920207 | 2.8 | −8.7 |
| Ni9 | 1 | 8/18 | 5.5 | 32.0 | N915070-N920207 | 2.6 | −8.3 |
| Ni9 | 1 | 9/2 | 5.5 | 32.0 | N915070-N920207 | 3.3 | −8.5 |
| Ni9 | 13 | 7/21 | 12.9 | 39.5 | N914284-N916129 | 2.6 | 8.3 |
| Ni9 | 13 | 8/18 | 12.9 | 39.5 | N914284-N916129 | 2.6 | 8.3 |
| Ni9 | 13 | 9/2 | 12.9 | 39.5 | N914284-N916129 | 2.6 | 7.4 |
| Ni9 | 14_1 | 6/23 | 97.3 | 53.4 | N901178-N900802 | 2.6 | 15.2 |
| Ni9 | 14_2 | 6/23 | 137.7 | 38.0 | N901524-N918080 | 5.2 | −21.3 |
| Ni9 | 14_2 | 7/21 | 137.7 | 38.0 | N901524-N918080 | 4.7 | −16.2 |

As shown in FIGS. 7 to 12, a marker located in the vicinity of the peak is inherited in linkage with a causative gene (or a group of causative genes) having the function of causing the improvement or reduction of smut resistance. This shows that the markers can be used as markers associated with resistance to sugarcane smut. Specifically, it has been revealed that the 85 types of markers shown in FIGS. 7 to 12 can be used as markers associated with resistance to sugarcane smut.

Figure 13:
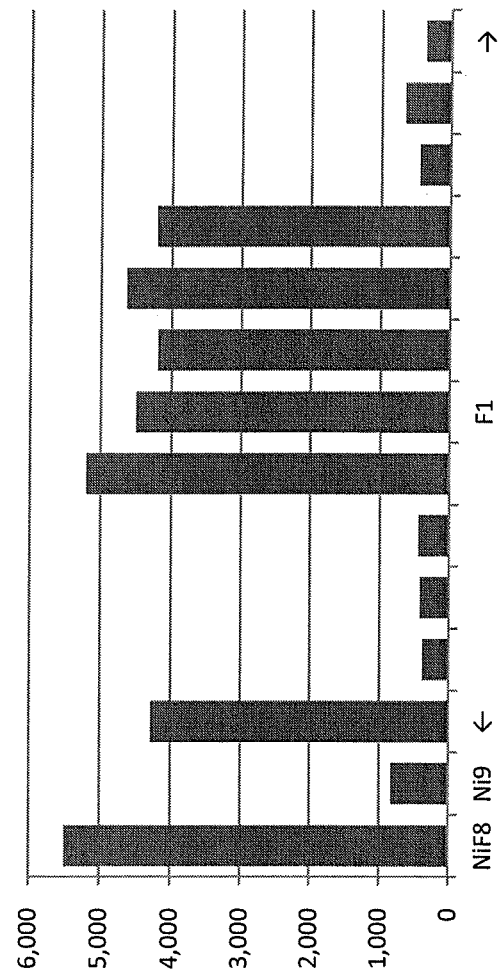
FIG. 13 is a characteristic chart showing signal levels of N802870 for individual lines.

In addition, as examples of signals detected in 2 (6) above, table 9 shows signal levels of 14 types of markers among markers N827337 to N821515 present in the 5th linkage group of NiF8 for NiF8 and Ni9 and their progeny lines. In particular, the signal levels of N802870 are shown in FIG. 13.

TABLE 9

| Linkage group | Marker name | NiF8 | Ni9 | | | | | F1 | | | | | | | |
|---|---|---|---|---|---|---|---|---|---|---|---|---|---|---|---|
| NiF8_5 | N827337 | 1,629 | 529 | 1,354 | 344 | 439 | 403 | 1,330 | 1,593 | 1,823 | 1,495 | 1,717 | 512 | 495 | 739 |
| | N802879 | 4,193 | 393 | 2,706 | 370 | 347 | 372 | 1,484 | 2,319 | 1,707 | 1,897 | 1,803 | 365 | 518 | 389 |
| | N804818 | 3,093 | 591 | 2,173 | 531 | 494 | 408 | 2,480 | 3,233 | 3,589 | 4,092 | 4,075 | 533 | 635 | 613 |
| | N816296 | 1,489 | 379 | 1,440 | 510 | 358 | 342 | 1,445 | 1,822 | 1,671 | 1,664 | 1,691 | 355 | 396 | 336 |
| | N804607 | 2,125 | 375 | 1,454 | 393 | 361 | 394 | 1,258 | 1,266 | 1,422 | 1,416 | 1,311 | 660 | 382 | 495 |
| | N802870 | 5,496 | 828 | 4,275 | 377 | 412 | 444 | 5,198 | 4,496 | 4,195 | 4,631 | 4,207 | 446 | 655 | 361 |
| | N813249 | 6,034 | 778 | 4,329 | 553 | 498 | 764 | 4,208 | 3,754 | 3,864 | 3,749 | 3,330 | 627 | 711 | 414 |
| | N813609 | 2,821 | 701 | 2,178 | 750 | 901 | 869 | 2,820 | 3,222 | 3,729 | 2,888 | 3,552 | 566 | 945 | 840 |
| | N815502 | 2,044 | 481 | 2,452 | 806 | 493 | 436 | 2,390 | 2,587 | 2,088 | 2,211 | 2,088 | 493 | 640 | 425 |
| | N815101 | 2,055 | 446 | 2,660 | 549 | 419 | 344 | 3,184 | 2,673 | 3,153 | 3,105 | 3,116 | 504 | 347 | 346 |
| | N823481 | 2,096 | 509 | 1,200 | 457 | 487 | 393 | 1,629 | 1,460 | 1,870 | 1,925 | 1,920 | 528 | 585 | 402 |
| | N801028 | 6,877 | 907 | 5,694 | 886 | 799 | 651 | 5,083 | 3,359 | 3,578 | 4,019 | 4,197 | 792 | 377 | 930 |
| | N810798 | 5,506 | 633 | 5,171 | 823 | 608 | 513 | 5,720 | 4,545 | 5,463 | 6,279 | 5,907 | 561 | 847 | 775 |
| | N821515 | 3,768 | 819 | 3,190 | 790 | 489 | 418 | 4,899 | 3,485 | 3,282 | 3,331 | 3,603 | 553 | 921 | 515 |

Signal levels of 14 types of markers were found to be remarkably high for progeny lines exhibiting reduction of smut resistance among the linkage groups present in NiF8. These results also revealed that 14 types of markers among markers N827337 to N821515 present in the 5th linkage group can be used as markers associated with resistance to sugarcane smut.

Figure 14:
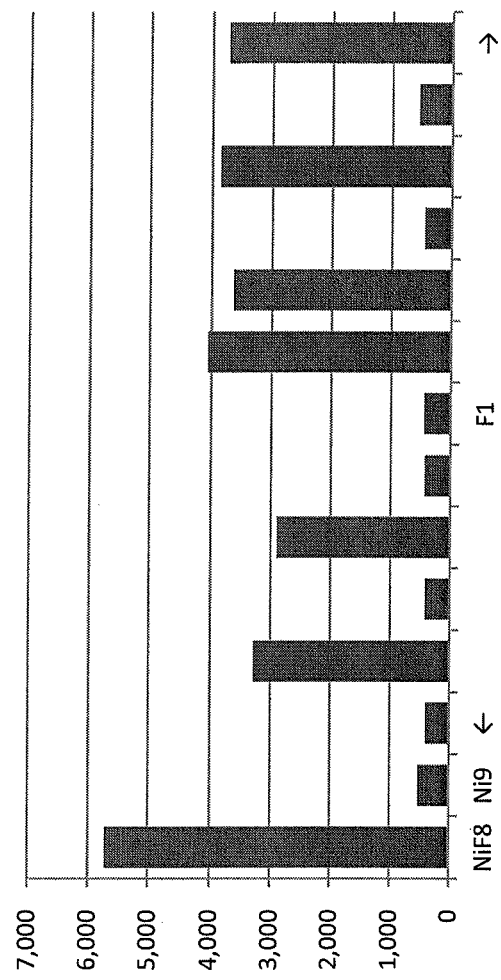
FIG. 14 is a characteristic chart showing signal levels of N827136 for individual lines.

Similarly, table 10 lists signal levels of 8 types of markers among markers N826561 to N826906 present in the 17th linkage group of NiF8 in NiF8 and Ni9 and the progeny lines. In particular, the signal levels of N827136 are shown in FIG. 14.

TABLE 10

| Linkage group | Marker name | NiF8 | Ni9 | | | | | | | | F1 | | | | | |
|---|---|---|---|---|---|---|---|---|---|---|---|---|---|---|---|---|
| NiF8_17 | N826561 | 1,977 | 525 | 462 | 1,514 | 574 | 1,629 | 744 | 864 | 1,136 | 1,415 | 528 | 1,752 | 453 | 1,350 |
| | N827136 | 5,717 | 514 | 390 | 3,279 | 405 | 2,898 | 423 | 433 | 4,050 | 3,633 | 445 | 3,857 | 547 | 3,723 |
| | N826325 | 1,620 | 404 | 421 | 1,103 | 358 | 1,102 | 381 | 408 | 1,081 | 1,409 | 408 | 1,458 | 381 | 1,317 |
| | N803928 | 2,082 | 403 | 390 | 1,517 | 427 | 1,875 | 412 | 426 | 1,696 | 1,520 | 393 | 1,743 | 322 | 1,620 |
| | N822568 | 3,592 | 501 | 753 | 2,556 | 466 | 2,502 | 360 | 506 | 2,159 | 2,941 | 425 | 2,733 | 571 | 2,580 |
| | N829026 | 1,766 | 540 | 432 | 1,656 | 452 | 1,759 | 396 | 656 | 2,159 | 2,325 | 456 | 1,906 | 558 | 2,041 |
| | N815300 | 3,128 | 669 | 708 | 1,951 | 974 | 2,189 | 460 | 439 | 2,271 | 1,981 | 687 | 2,039 | 372 | 2,028 |
| | N826906 | 2,339 | 447 | 407 | 1,704 | 754 | 2,139 | 679 | 485 | 2,122 | 2,554 | 361 | 1,915 | 480 | 2,281 |

Signal levels of 8 types of markers were found to be remarkably high for progeny lines exhibiting excellent smut resistance among the linkage groups present in NiF8. These results also revealed that 8 types of markers among markers N826561 to N826906 present in the 17th linkage group can be used as markers associated with resistance to sugarcane smut.

Figure 15:
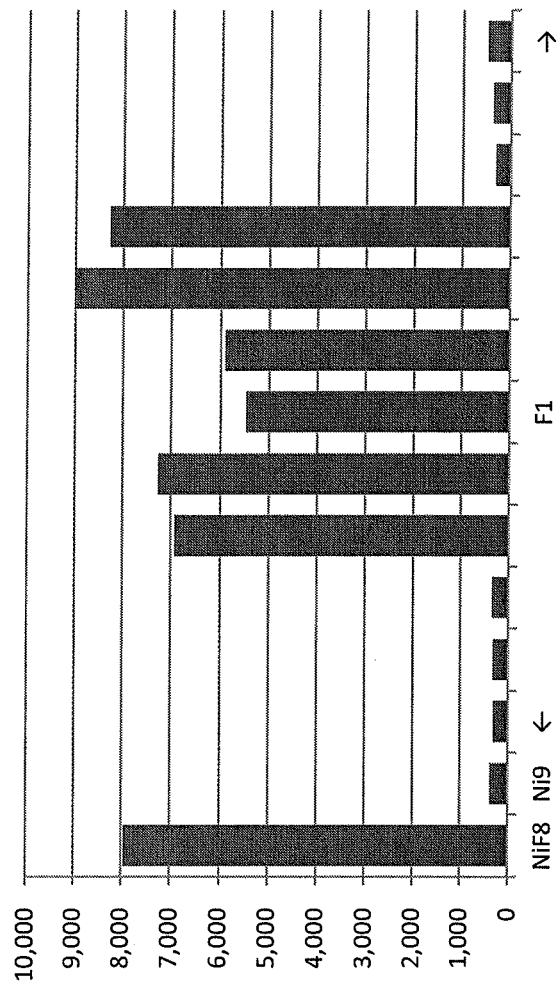
FIG. 15 is a characteristic chart showing signal levels of N812680 for individual lines.

Similarly, table 11 lists signal levels of 10 types of markers among markers N816552 to N821999 present in the 40th linkage group of NiF8 in NiF8 and Ni9 and the progeny lines. In particular, the signal levels of N812680 are shown in FIG. 15.

TABLE 11

| Linkage group | Marker name | NiF8 | Ni9 | | | | | | | | F1 | | | | | |
|---|---|---|---|---|---|---|---|---|---|---|---|---|---|---|---|---|
| NiF8_40 | N816552 | 2,731 | 770 | 630 | 622 | 845 | 3,929 | 4,570 | 4,215 | 3,666 | 4,651 | 4,394 | 900 | 719 | 747 |
| | N827448 | 2,470 | 450 | 357 | 391 | 340 | 2,664 | 3,031 | 2,325 | 2,650 | 2,035 | 2,473 | 376 | 564 | 467 |
| | N829378 | 3,344 | 609 | 443 | 505 | 453 | 1,508 | 2,045 | 2,319 | 1,428 | 1,093 | 1,506 | 752 | 603 | 497 |
| | N829404 | 2,700 | 752 | 723 | 758 | 771 | 2,641 | 2,295 | 2,645 | 2,128 | 2,792 | 3,259 | 523 | 748 | 794 |
| | N828725 | 2,053 | 461 | 548 | 542 | 433 | 1,860 | 2,282 | 2,130 | 1,645 | 2,066 | 1,435 | 496 | 368 | 453 |
| | N812680 | 7,958 | 377 | 309 | 322 | 343 | 6,921 | 7,267 | 5,468 | 5,905 | 9,015 | 8,278 | 317 | 378 | 490 |
| | N811688 | 4,885 | 410 | 680 | 954 | 496 | 3,324 | 4,237 | 3,073 | 2,636 | 2,919 | 3,384 | 520 | 471 | 649 |
| | N819703 | 4,612 | 736 | 617 | 820 | 633 | 4,054 | 5,138 | 3,636 | 5,267 | 5,107 | 3,622 | 761 | 648 | 907 |
| | N815648 | 3,391 | 471 | 472 | 550 | 363 | 2,902 | 3,116 | 2,694 | 2,747 | 3,836 | 3,554 | 393 | 680 | 483 |
| | N821999 | 3,255 | 678 | 427 | 422 | 427 | 2,959 | 2,237 | 3,538 | 2,036 | 2,680 | 3,002 | 904 | 413 | 401 |

Signal levels of 10 types of markers were found to be remarkably high for progeny lines exhibiting reduction of smut resistance among the linkage groups present in NiF8. 40 These results also revealed that 10 types of markers among markers N816552 to N821999 present in the 40th linkage group can be used as markers associated with resistance to sugarcane smut.

Figure 16:
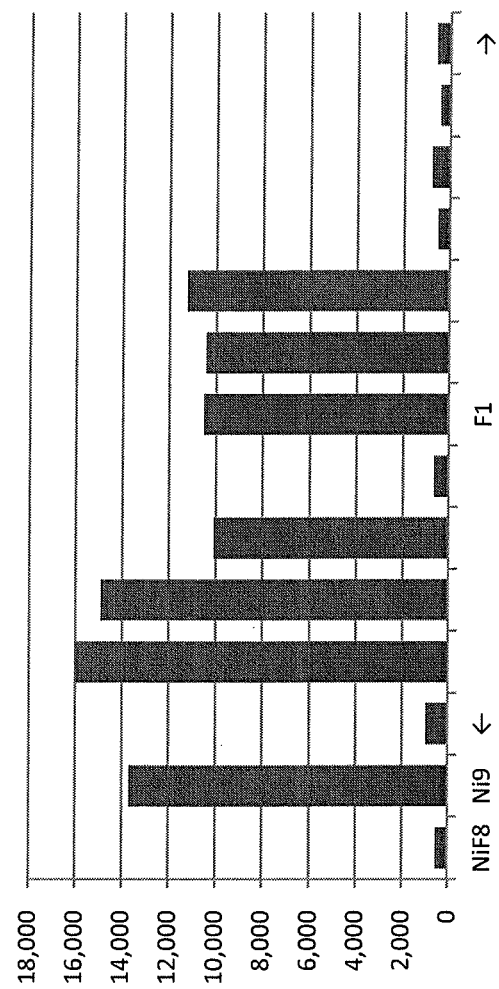
FIG. 16 is a characteristic chart showing signal levels of N916081 for individual lines.

Similarly, table 12 lists signal levels of 19 types of markers among markers N915070 to N920207 present in the 1st linkage group of Ni9 in NiF8 and Ni9 and the progeny lines. In particular, the signal levels of N916081 are shown in FIG. 16.

TABLE 12

| Linkage group | Marker name | NiF8 | Ni9 | | | | | | | | F1 | | | | | |
|---|---|---|---|---|---|---|---|---|---|---|---|---|---|---|---|---|
| Ni9_1 | N915070 | 424 | 1,195 | 418 | 1,393 | 1,122 | 1,717 | 480 | 1,356 | 1,359 | 1,707 | 370 | 424 | 424 | 403 |
| | N915209 | 560 | 1,796 | 435 | 2,840 | 1,778 | 3,016 | 601 | 2,376 | 2,361 | 3,451 | 446 | 541 | 462 | 484 |
| | N916186 | 496 | 2,002 | 403 | 2,447 | 1,808 | 1,571 | 415 | 2,608 | 1,723 | 2,687 | 406 | 671 | 466 | 432 |
| | N902342 | 372 | 1,245 | 349 | 1,049 | 1,003 | 1,045 | 420 | 1,062 | 1,346 | 2,206 | 333 | 352 | 401 | 398 |
| | N919949 | 625 | 1,459 | 406 | 2,169 | 1,942 | 2,723 | 738 | 1,679 | 2,360 | 3,490 | 650 | 680 | 444 | 572 |
| | N920597 | 450 | 4,702 | 399 | 5,028 | 3,819 | 5,583 | 348 | 6,733 | 4,669 | 7,196 | 436 | 431 | 393 | 537 |
| | N916081 | 516 | 13,678 | 954 | 16,011 | 14,893 | 10,082 | 634 | 10,528 | 10,441 | 11,232 | 504 | 785 | 435 | 604 |
| | N902047 | 955 | 5,233 | 658 | 4,400 | 3,853 | 4,711 | 825 | 3,378 | 5,336 | 6,194 | 581 | 992 | 555 | 854 |
| | N916874 | 491 | 3,320 | 486 | 2,511 | 2,869 | 3,276 | 708 | 2,304 | 3,046 | 4,073 | 416 | 791 | 409 | 430 |
| | N918161 | 438 | 2,109 | 411 | 1,989 | 1,892 | 2,109 | 397 | 1,690 | 2,193 | 2,643 | 406 | 610 | 398 | 335 |
| | N918536 | 372 | 1,059 | 508 | 1,229 | 1,293 | 1,368 | 487 | 1,253 | 1,704 | 1,967 | 511 | 423 | 395 | 381 |
| | N901676 | 648 | 1,534 | 702 | 2,407 | 1,395 | 1,389 | 705 | 1,590 | 1,820 | 1,918 | 521 | 577 | 483 | 582 |
| | N919743 | 635 | 2,361 | 437 | 1,703 | 1,731 | 1,990 | 471 | 2,385 | 2,076 | 3,665 | 568 | 417 | 399 | 398 |
| | N901176 | 697 | 5,017 | 408 | 3,009 | 5,027 | 5,059 | 820 | 5,316 | 3,362 | 3,347 | 764 | 454 | 715 | 420 |
| | N916035 | 757 | 4,444 | 684 | 3,088 | 3,803 | 3,576 | 580 | 4,310 | 4,270 | 4,272 | 448 | 585 | 485 | 581 |
| | N921010 | 521 | 5,630 | 448 | 6,214 | 5,012 | 7,792 | 909 | 5,074 | 4,902 | 5,904 | 557 | 658 | 559 | 611 |
| | N915635 | 424 | 7,875 | 538 | 12,542 | 10,900 | 15,388 | 568 | 9,698 | 10,501 | 14,732 | 391 | 505 | 400 | 469 |

TABLE 12-continued

| Linkage group | Marker name | NiF8 | Ni9 | | | | | F1 | | | | | | |
|---|---|---|---|---|---|---|---|---|---|---|---|---|---|---|
| | N901348 | 493 | 3,188 | 558 | 6,692 | 7,451 | 6,466 | 605 | 3,553 | 7,406 | 2,655 | 659 | 584 | 638 | 438 |
| | N920207 | 421 | 5,291 | 349 | 4,550 | 4,857 | 6,695 | 385 | 1,962 | 3,567 | 11,697 | 449 | 478 | 416 | 450 |

Signal levels of 19 types of markers were found to be remarkably high for progeny lines exhibiting excellent smut resistance among the linkage groups present in Ni9. These results also revealed that 19 types of markers among markers N915070 to N920207 present in the 1st linkage group can be used as markers associated with resistance to sugarcane smut.

Figure 17:
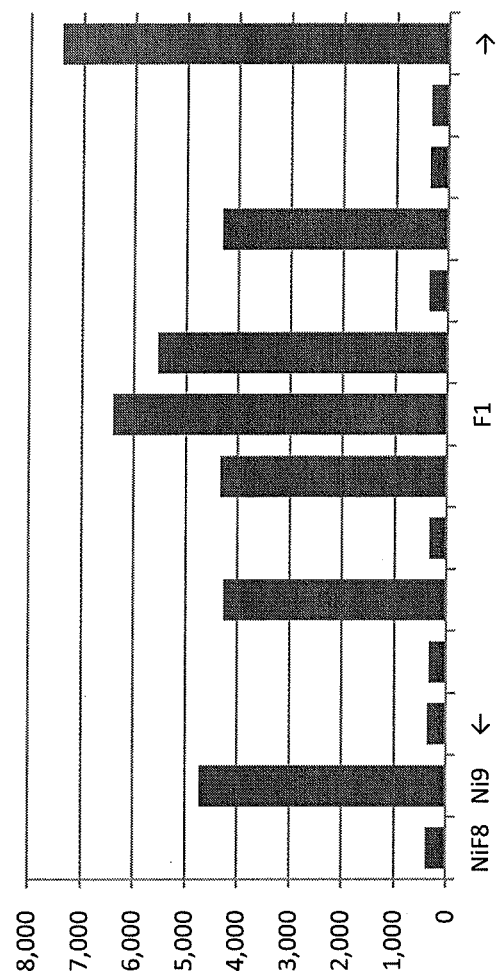
FIG. 17 is a characteristic chart showing signal levels of N919839 for individual lines.

Similarly, table 13 lists signal levels of 11 types of markers among markers N914284 to N916129 present in the 13th linkage group of Ni9 in NiF8 and Ni9 and the progeny lines. In particular, the signal levels of N919839 are shown in FIG. 17.

TABLE 13

| Linkage group | Marker name | NiF8 | Ni9 | | | | | F1 | | | | | | |
|---|---|---|---|---|---|---|---|---|---|---|---|---|---|---|
| Ni9_13 | N914284 | 439 | 1,102 | 380 | 551 | 1,358 | 562 | 1,234 | 1,463 | 1,247 | 877 | 1,235 | 492 | 467 | 1,342 |
| | N901453 | 788 | 1,511 | 661 | 638 | 1,120 | 560 | 1,380 | 2,056 | 2,671 | 807 | 1,415 | 512 | 533 | 1,821 |
| | N900044 | 688 | 1,693 | 646 | 652 | 1,600 | 554 | 1,632 | 2,841 | 2,410 | 618 | 1,619 | 603 | 577 | 1,639 |
| | N919839 | 389 | 4,719 | 364 | 329 | 4,261 | 332 | 4,331 | 6,387 | 5,540 | 360 | 4,307 | 352 | 334 | 7,400 |
| | N901567 | 426 | 2,890 | 374 | 399 | 3,213 | 526 | 3,981 | 5,253 | 5,212 | 434 | 3,364 | 449 | 383 | 4,346 |
| | N911103 | 500 | 902 | 388 | 424 | 1,069 | 414 | 1,246 | 2,352 | 1,465 | 408 | 1,036 | 417 | 630 | 1,500 |
| | N918508 | 686 | 5,836 | 513 | 667 | 4,963 | 778 | 4,317 | 7,106 | 5,911 | 599 | 4,037 | 587 | 547 | 7,786 |
| | N918344 | 385 | 1,970 | 352 | 578 | 1,765 | 470 | 2,000 | 3,298 | 2,428 | 409 | 2,079 | 426 | 483 | 2,488 |
| | N919696 | 497 | 2,696 | 496 | 427 | 2,327 | 685 | 1,928 | 2,433 | 2,370 | 414 | 2,043 | 680 | 657 | 2,763 |
| | N916172 | 471 | 1,960 | 448 | 378 | 3,025 | 445 | 2,990 | 4,282 | 3,314 | 433 | 2,666 | 403 | 445 | 3,518 |
| | N916129 | 526 | 5,026 | 641 | 506 | 3,393 | 858 | 3,465 | 5,094 | 5,261 | 478 | 4,030 | 383 | 558 | 6,621 |

Signal levels of 11 types of markers were found to be remarkably high for progeny lines exhibiting reduction of smut resistance among the linkage groups present in Ni9. These results also revealed that 11 types of markers among markers N914284 to N916129 present in the 13th linkage group can be used as markers associated with resistance to sugarcane smut.

Figure 18:
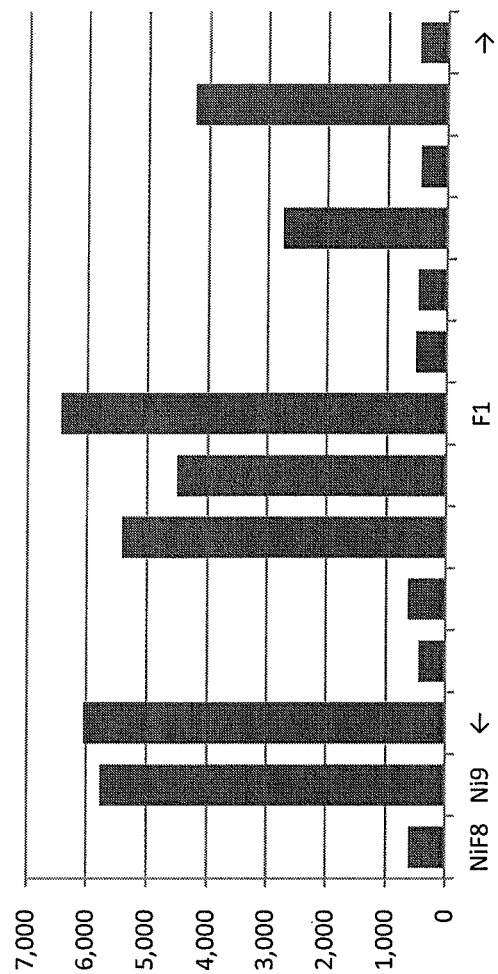
FIG. 18 is a characteristic chart showing signal levels of N918761 for individual lines.

Similarly, table 14 lists signal levels of 10 types of markers among markers N901178 to N900802 present in the 14th linkage group of Ni9 in NiF8 and Ni9 and the progeny lines. In particular, the signal levels of N918761 are shown in FIG. 18.

TABLE 14

| Linkage group | Marker name | NiF8 | Ni9 | | | | | F1 | | | | | | |
|---|---|---|---|---|---|---|---|---|---|---|---|---|---|---|
| Ni9_14_1 | N901178 | 617 | 1,779 | 1,250 | 508 | 414 | 1,929 | 1,698 | 1,986 | 470 | 584 | 1,104 | 498 | 1,454 | 539 |
| | N918761 | 607 | 5,766 | 6,048 | 453 | 631 | 5,410 | 4,505 | 6,440 | 519 | 484 | 2,747 | 453 | 4,233 | 473 |
| | N913735 | 850 | 2,996 | 2,251 | 557 | 519 | 2,576 | 2,759 | 3,188 | 496 | 555 | 1,903 | 461 | 2,490 | 651 |
| | N900663 | 686 | 3,173 | 2,014 | 412 | 466 | 2,351 | 3,156 | 4,168 | 475 | 423 | 1,810 | 559 | 2,534 | 662 |
| | N918363 | 477 | 1,964 | 1,961 | 573 | 481 | 1,895 | 2,092 | 2,809 | 516 | 486 | 2,012 | 496 | 2,223 | 583 |
| | N918213 | 760 | 2,319 | 3,224 | 882 | 798 | 3,485 | 3,433 | 4,402 | 579 | 507 | 3,767 | 678 | 2,874 | 509 |
| | N900568 | 1,040 | 3,437 | 3,017 | 581 | 368 | 2,479 | 3,246 | 3,387 | 571 | 476 | 2,088 | 525 | 1,821 | 833 |
| | N912523 | 626 | 6,398 | 6,371 | 476 | 565 | 4,799 | 5,756 | 7,064 | 526 | 813 | 4,739 | 424 | 4,431 | 541 |
| | N900344 | 692 | 5,788 | 6,366 | 838 | 759 | 3,590 | 5,674 | 6,474 | 588 | 729 | 6,622 | 640 | 5,622 | 542 |
| | N900802 | 717 | 6,090 | 6,668 | 453 | 537 | 4,639 | 6,414 | 8,043 | 618 | 905 | 5,322 | 430 | 6,032 | 619 |

Signal levels of 10 types of markers were found to be remarkably high for progeny lines exhibiting reduction of smut resistance among the linkage groups present in Ni9. These results also revealed that 10 types of markers among markers N901178 to N900802 present in the 14th linkage group can be used as markers associated with resistance to sugarcane smut.

Figure 19:
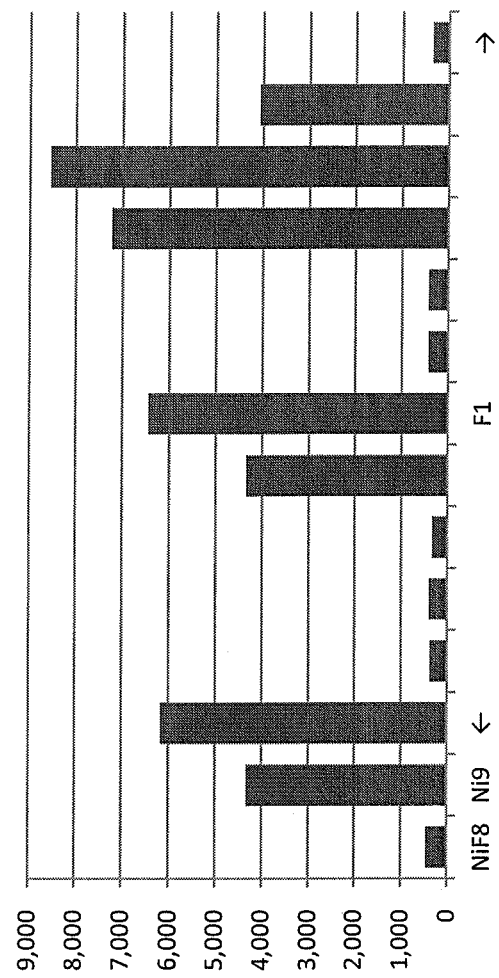
FIG. 19 is a characteristic chart showing signal levels of N901160 for individual lines.

Similarly, table 15 lists signal levels of 13 types of markers among markers N901524 to N918080 present in the 14th linkage group of Ni9 in NiF8 and Ni9 and the progeny lines. In particular, the signal levels of N901160 are shown in FIG. 19.

TABLE 15

| Linkage group | Marker name | NiF8 | Ni9 | F1 | | | | | | | | | | | |
|---|---|---|---|---|---|---|---|---|---|---|---|---|---|---|---|
| Ni9_14_2 | N901524 | 428 | 2,677 | 2,763 | 425 | 457 | 343 | 2,534 | 1,954 | 617 | 445 | 3,083 | 1,291 | 2,532 | 674 |
| | N901163 | 379 | 3,462 | 2,099 | 909 | 861 | 632 | 3,268 | 3,426 | 600 | 380 | 3,196 | 3,202 | 3,260 | 392 |
| | N911063 | 575 | 4,326 | 5,570 | 385 | 466 | 384 | 2,738 | 7,453 | 398 | 409 | 7,625 | 8,794 | 2,220 | 381 |
| | N914692 | 625 | 3,592 | 4,016 | 811 | 577 | 419 | 3,574 | 3,955 | 742 | 959 | 3,573 | 4,756 | 4,094 | 714 |
| | N911405 | 386 | 1,893 | 1,692 | 470 | 404 | 411 | 1,715 | 2,402 | 411 | 437 | 1,762 | 2,052 | 1,660 | 396 |
| | N913383 | 580 | 2,923 | 2,202 | 710 | 421 | 596 | 2,256 | 2,986 | 821 | 798 | 2,768 | 3,336 | 2,062 | 708 |
| | N914112 | 564 | 3,387 | 3,390 | 825 | 417 | 730 | 1,913 | 3,528 | 1,000 | 987 | 2,934 | 3,753 | 2,600 | 966 |
| | N915180 | 537 | 2,482 | 2,950 | 566 | 485 | 396 | 2,590 | 2,968 | 438 | 497 | 2,242 | 3,021 | 3,110 | 729 |
| | N901160 | 452 | 4,333 | 6,165 | 375 | 394 | 333 | 4,340 | 6,432 | 424 | 417 | 7,227 | 8,545 | 4,069 | 359 |
| | N916293 | 560 | 2,069 | 1,908 | 725 | 868 | 520 | 1,420 | 3,179 | 463 | 517 | 1,720 | 2,129 | 1,681 | 464 |
| | N916263 | 414 | 2,358 | 1,775 | 379 | 348 | 359 | 2,136 | 2,174 | 522 | 404 | 2,041 | 1,850 | 2,502 | 491 |
| | N917579 | 485 | 2,335 | 1,873 | 501 | 459 | 395 | 2,209 | 3,210 | 440 | 390 | 2,959 | 1,816 | 3,724 | 378 |
| | N918080 | 469 | 1,238 | 1,171 | 432 | 532 | 361 | 1,621 | 1,567 | 380 | 402 | 1,269 | 1,015 | 1,940 | 442 |

Signal levels of 13 types of markers were found to be remarkably high for progeny lines exhibiting excellent smut resistance among the linkage groups present in Ni9. These results also revealed that 13 types of markers among markers N901524 to N918080 present in the 14th linkage group can be used as markers associated with resistance to sugarcane smut.

All publications, patents, and patent applications cited herein are incorporated herein by reference in their entirety.

---

The invention claimed is:

1. A method for producing a sugarcane line having improved smut resistance, said method comprising:
   extracting genomic DNA from a progeny plant obtained from parent plants, at least one of which is a sugarcane plant, and/or a genomic DNA of a parent sugarcane plant;
   determining by nucleic acid assay the presence of a marker associated with resistance to sugarcane smut in the obtained genomic DNA, and selecting the progeny plant as a plant having improved smut resistance based on the presence of said marker; and
   using the selected plant as a parent plant for crossing, to thereby produce progeny plant(s),
   wherein said marker consists of a continuous nucleic acid region in the obtained genomic DNA, and wherein said marker comprises at least 20 continuous nucleotides of a nucleotide sequence selected from the group consisting of SEQ ID NOs: 19 to 22.

2. The method for producing a sugarcane line according to claim 1, wherein a DNA chip that comprises a probe corresponding to the marker associated with resistance to sugarcane smut is used in the determination step.

3. The method for producing a sugarcane line according to claim 1, wherein the progeny plant used in said genomic DNA extracting step is in the form of seeds or a young seedling, and the genomic DNA is extracted from the seeds or the young seedling.

4. The method for producing a sugarcane line according to claim 1, wherein the progeny plant(s) produced using the selected plant as a parent plant for crossing is in the form of seeds or a young seedling.

* * * * *